United States Patent
Stein et al.

(10) Patent No.: US 6,258,774 B1
(45) Date of Patent: Jul. 10, 2001

(54) CARRIER FOR IN VIVO DELIVERY OF A THERAPEUTIC AGENT

(75) Inventors: Stanley Stein, East Brunswick; Michael J. Leibowitz, Manalapan; Patrick J. Sinko, Lebanon, all of NJ (US)

(73) Assignee: University of Medicine and Dentistry of New Jersey, Piscataway, NJ (US)

( * ) Notice: Subject to any disclaimer, the term of this patent is extended or adjusted under 35 U.S.C. 154(b) by 0 days.

(21) Appl. No.: 09/044,411

(22) Filed: Mar. 19, 1998

(51) Int. Cl.[7] .......................... A61K 38/08; A61K 47/30; C07K 7/06
(52) U.S. Cl. ..................... 514/2; 514/15; 525/50; 525/403; 530/327; 530/345; 530/408
(58) Field of Search .............................. 424/179.1, 180.1, 424/181.1, 194.1, 94.3; 435/188; 514/2, 15; 530/327, 328, 345, 391.3, 391.5, 391.7, 391.9, 404, 408; 525/50, 403, 430; 528/421, 491

(56) References Cited

U.S. PATENT DOCUMENTS

| | | | |
|---|---|---|---|
| 4,479,940 | * 10/1984 | Bizzini | 424/177 |
| 5,219,564 | 6/1993 | Zalipsky et al. | 424/78.17 |
| 5,264,221 | * 11/1993 | Tagawa et al. | 424/450 |
| 5,274,122 | * 12/1993 | Tolman et al. | 349/6 |
| 5,276,140 | * 1/1994 | Nitecki et al. | 530/391.71 |
| 5,455,027 | 10/1995 | Zalipsky et al. | 424/78.17 |
| 5,679,527 | * 10/1997 | Humphreys | 435/7.1 |
| 5,738,855 | * 4/1998 | Szu et al. | 424/258.1 |
| 6,025,140 | * 2/2000 | Langel et al. | 435/6 |
| 6,046,305 | * 4/2000 | Choi | 528/491 |
| 6,093,692 | * 7/2000 | Shen et al. | 514/3 |

FOREIGN PATENT DOCUMENTS

WO 98/47913 10/1998 (WO).

OTHER PUBLICATIONS

Musu et al., 1996, Appl Biochem Biotechnol, 56:243–63.
Davis et al, 1981, Clin Exp Immunol, 46:649–52.
Duncan et al, 1984, Adv Polym Sci, 57:53–101.
Goff et al, Biocon Chem., 1:381–6 (1990).
Grassetti et al, 1967, Arch Biochem Biophys, 119:41–9.
Meister et al, 1991, Pharmacol Ther, 51:155–94.
Meister et al, Ciba Foundation Symposium, 72:135–61 (1980).
Nathan et al, 1993, Bioconj Chem, 4:54–62.
Trimble et al, 1997, Bioconj Chem, 8:416–23.
Woghiren et al, 1993, Biocon Chem, 4:314–8.
Huang et al., 1998, Bioconjugate Chem, 9:612–7.
Copy of provisional application 60/069,525, Dec. 12, 1997.*
Grant. Hackh's Chemical Dictionary, 4th ed. New York:McGraw–Hill Book Co. p. 534, 1972.*
Carlsson et al, Protein Thiolation and Reversible . . . Biochem. J. vol. 173, pp. 723–737, 1978.*

* cited by examiner

Primary Examiner—Jeffrey E. Russel
(74) Attorney, Agent, or Firm—Klauber & Jackson

(57) ABSTRACT

A carrier for in vivo delivery of a therapeutic agent comprising a thiol group is provided, wherein the therapeutic agent is conjugated to the carrier via a biodegradable disulfide bond. Since extracellular fluids in vivo do not provide the appropriate environment to efficiently reduce a disulfide bond, while cellular cytosol does provide an appropriate environment, the agent will remain substantially coupled to the carrier while circulating through the body until the carrier crosses a cell membrane. As a result, the therapeutic agent is protected from degradation and renal clearance, and the potential for the therapeutic agent to elicit an immune response is limited.

111 Claims, 7 Drawing Sheets

Scheme I

Scheme II

CARRIER FOR IN VIVO DELIVERY OF A THERAPEUTIC AGENT

FIELD OF THE INVENTION

The invention relates to chemical compounds for delivering therapeutic agents to tissues of a mammal, such as a human. More particularly, the invention involves a carrier for delivery of a therapeutic agent in which a biodegradable disulfide bond conjugates the therapeutic agent to a carrier of the present invention. The disulfide bond can be reduced in an appropriate environment in vivo so that a greater amount of the therapeutic agent is neither degraded nor excreted, but can be delivered to tissues, thus increasing its therapeutic effectiveness.

BACKGROUND OF THE INVENTION

It has been proposed that compounds, such as peptides, peptide mimetics, and oligonucleotides, or analogs or derivatives thereof, can be used as potential therapeutic agents. However, problems have been encountered in administering such compounds to a subject. For example, proteases and endonucleases present throughout the body digest such compounds, severely decreasing their biological activity. Other problems involve the elicitation of an immune response against the compound resulting in the degradation and inactivation of such compounds, and rapid renal clearance, particularly if the therapeutic agent has a low molecular weight. Hence, in order to be effective, such therapeutic agents must be administered frequently, and parenterally rather than orally. An example of such a therapeutic agent is insulin, which is typically injected several times daily by diabetics.

In efforts to overcome these problems, researchers have attempted to modify chemically such therapeutic agents in order to manipulate their pharmacologic properties[1], and perhaps enable them to survive longer in vivo before being degraded and removed from the blood stream. For example, one method of chemically modifying therapeutics is to append water-soluble polymer chains, such as polyethylene glycol (PEG), to the therapeutic agent[2]. Researchers have designed a PEG-lysine copolymer having multiple attachment sites[3], and have conjugated the copolymer to low molecular weight therapeutic agents. However, such modifications have inherent limitations. For example, they frequently interfere with the bioavailability of the therapeutic. Consequently, if the target for a therapeutic agent is intracellular, and the modification of the therapeutic prevents its crossing of the cell membrane, then the bioavailability of the therapeutic agent is reduced due to the chemical modification.

Another limitation to attaching a water-soluble polymer to a therapeutic agent involves modulating the biological activity of the therapeutic agent in a deleterious manner. For example, if the modification of the therapeutic agent alters its three dimensional structure, then its ability to bind a receptor site it was designed to bind can be decreased, resulting in a decrease of activity.

Hence, what is needed is a carrier of a therapeutic agent that reduces the chance of an elicitation of an immune response against the therapeutic agent.

Moreover, what is needed is a carrier that protects therapeutic agents from protease/peptidase/nuclease degradation in vivo, thereby eliminating the need for repetitive administration of the therapeutic agent.

In addition, what is needed is a carrier of a therapeutic agent that enhances cellular transmembrane delivery of the therapeutic agent.

Also, what is needed is a carrier of a therapeutic agent that does not release the therapeutic agent until the carrier has crossed the cell membrane, and once inside the cell, the carrier can release the therapeutic agent in a biologically active state.

What is also needed is a carrier of a therapeutic agent that does not interfere with the bioavailability of the therapeutic agent.

SUMMARY OF THE INVENTION

There is provided, in accordance with the present invention, a carrier for in vivo delivery of therapeutic agents that does not possess the shortcomings of other drug delivery carriers as described above, and offers the advantages of not interfering with the bioavailability of a therapeutic agent, protecting the therapeutic agent from proteolytic/nucleolytic degradation, from eliciting an immune response, and from rapid renal clearance, to name only a few.

Broadly, the present invention provides a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond. The disulfide bond can be broken in a physiologically relevant reducing environment, such as that found in the cytosol of a cell. Hence, Applicants have discovered a way to modify a therapeutic agent to minimize degradation in vivo, and yet not limit its bioavailability. In addition, the present invention is particularly well suited to deliver therapeutic agents to the cytosol of cells. Glutathione, a naturally occurring reducing agent is found predominantly in cell cytosol. Hence, glutathione can reduce a disulfide bond, and release a therapeutic agent from a carrier of the present invention within the cells of the target tissue. In addition, since more than one thiol compound can be conjugated to the polymer, the carrier of the present invention can deliver more than one molecule of therapeutic agent to a target cell or tissue.

Numerous therapeutic agents comprise thiol groups, and can be used to conjugate the therapeutic agent to a carrier of the present invention with a disulfide bond. For example, therapeutic agents which are peptides comprising a cysteine residue can be delivered in vivo with a carrier of the present invention. In addition, analogs or derivatives of peptides which serve as therapeutic agents can be made to comprise a thiol group so that they can be delivered in vivo with a carrier of the present invention. Even nucleotides and analogs or derivatives thereof, used in antisense therapy for example, can be easily modified to comprise a thiol group in order to be carried via a carrier of the present invention.

Another example of a therapeutic agent comprising a thiol group, which can be conjugated to a a carrier of the present invention for in vivo delivery, is a therapeutic agent which inhibits HIV-1 replication. More specifically, it has been determined that the HIV Tat protein strongly activates HIV transcription through its interactions with the TAR RNA region. The TAR RNA domain consists of the first 57 nucleotides of all virally encoded RNAs. The predicted TAR RNA secondary structure is a double-stranded stem with a 3-base bulge and a 6-base loop. HIV-1 Tat is a small nuclear protein containing 86–102 amino acids, and is encoded by multiply spliced mRNA. The 3-base bulge in TAR RNA and several other flanking nucleotides are essential for Tat-TAR interaction.

Tat protein apparently acts to promote transcription by binding through its basic domain to the 3-base bulge of TAR.

This is accompanied by recruitment of host cellular factors, including Tat and TAR binding proteins, to the TAR RNA stem and 6-base loop, as well as to the complex of template DNA, transcription factors and RNA polymerase. Initiation of proviral gene expression appears to occur by activation of an NF-κB and/or Sp1-dependent promoter, resulting in production of viral transcripts at a sufficient level to provide synthesis of Tat protein, which then interacts with TAR to allow enhanced production of elongated HIV transcripts.

Efforts have been made to develop a therapeutic agent which binds TAR, and blocks Tat-TAR binding. For example, a 10-residue Tat peptide with an appended 4-mer antisense oligonucleotide can specifically bind to TAR RNA, as shown by its ability to stimulate RNase H-mediated cleavage at the site of oligonucleotide annealing to the 6-base single-stranded loop. In another example, a biotinylated peptide has also been shown to inhibit Tat binding to TAR (please see Choudhury, I., Wang, J., Rabson, A. B., Stein, S., Pooyan, S., Stein, S. and Leibowitz, M. J. (1998) Inhibition of HIV-1 replication by a Tat RNA binding domain peptide analog. *J. Acqu. Immune Def. Syndr. & Human Retrovirol.*, 17, 104–111, incorporated by reference herein in its entirety).

Hence, the present invention extends to a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, and the therapeutic agent is a Tat inhibitory polypeptide derivative. More particularly, in an embodiment of the invention, a therapeutic agent comprising a thiol group, which is a Tat-inhibitory binding peptide derivative, relates to biotinylated peptides of the formula I:

R-Arg-Lys-Lys-Arg-Arg-Gln-Arg-Arg-Arg-X-(biotin)-Cys-NH$_2$ (SEQ ID NO: 1)

wherein R is the residue of the carboxylic acid, or an acetyl group, and X is a Cys or Lys residue, and analogs thereof, and biologically and pharmaceutically acceptable salts thereof, all stereo, optical and geometrical isomers thereof where such isomers exist, as well as the pharmaceutically acceptable salts and solvates thereof, which exhibit advantageous properties, including binding to ΔTAR, inhibition of LTR-dependent reporter gene expression in a model cell assay and, finally, inhibition of HIV-1 replication, as determined as assays of HIV-induced syncytium formation, cytotoxicity and reverse transcriptase production. The biotinylated peptide of formula I can be readily conjugated to a carrier of the present invention via a disulfide bond between the sulfur of the thiol group of a Cys residue and the sulfur of the thiol group of the thiol compound of the carrier. Examples of such Tat peptide derivatives include, but are not limited to:

N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO:3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO:5)
N-acetyl-Gln-Lys-Lys-Arg-Arg-Gln-Arg-Arg-Arg-D-Lys-(biotin)-Cys-NH$_2$ (SEQ ID NO:6)
N-acetyl-Arg-Lys-Lys-Arg-Arg-Pro-Arg-Arg-Arg-Cys-(biotin)-Cys-NH$_2$ (SEQ ID NO:7).

In another embodiment, the present invention extends to a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, and the therapeutic agent is a Tat inhibitory polypeptide derivative comprising an amino acid sequence of:

N-acetyl-DCys-DLys-(biotin)-DArg-DArg-DArg-DGln-DArg-DArg-DLys-DLys-DArg-NH$_2$ (SEQ ID NO:8)

or analogs or derivatives thereof, and biologically and pharmaceutically acceptable salts thereof, which exhibit advantageous properties, including binding to ΔTAR, inhibition of LTR-dependent reporter gene expression in a model cell assay and, finally, inhibition of HIV-1 replication.

Furthermore, the present invention extends to a method of treating a viral infection in a mammal in need of such treatment. More particularly, such a method comprises administering to a mammal a therapeutically effective amount of a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, and the therapeutic agent comprises a Tat-inhibitory binding peptide derivative which comprises a biotinylated peptide of the formula I:

R-Arg-Lys-Lys-Arg-Arg-Gln-Arg-Arg-Arg-X-(biotin)-Cys-NH$_2$ (SEQ ID NO:1)

wherein R is the residue of a carboxylic acid or acetyl group, X is a Cys or Lys residue, analogs thereof, and biologically and pharmaceutically acceptable salts thereof. Throughout the specification and appended claims, the polypeptide of formula I, and its analogs and salts, encompass all stereo, optical and geometrical isomers thereof where such isomers exist, as well as the pharmaceutically acceptable salts and solvates thereof. Where appropriate, the polypeptide or its analogs can be utilized as its corresponding amide form. The amino acid residues described herein are preferred to be in the "L" isomeric form. However, residues in the "D" isomeric form can be substituted for any L-amino acid residue, as long as the desired functional property is retained by the polypeptide.

More particularly, a therapeutic agent having applications in such a method comprises an amino acid sequence including, but not limited to:

N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO: 3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO.-5)
N-acetyl-Gln-Lys-Lys-Arg-Arg-Gln-Arg-Arg-Arg-D-Lys-(biotin)-Cys-NH$_2$ (SEQ ID NO:6)
N-acetyl-Arg-Lys-Lys-Arg-Arg-Pro-Arg-Arg-Arg-Cys-(biotin)-Cys-NH$_2$ (SEQ ID NO:7).

In another embodiment, the present invention extends to a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, and the therapeutic agent is a Tat inhibitory polypeptide derivative comprising an amino acid sequence as set forth below:

N-acetyl-DCys-DLys-(biotin)-DArg-DArg-DArg-DGln-DArg-DArg-DLys-DLys-DArg-NH$_2$ (SEQ ID NO:8)

or analogs or derivatives thereof, and biologically and pharmaceutically acceptable salts thereof, which exhibit advantageous properties, including binding to ΔTAR, inhibition of LTR-dependent reporter gene expression in a model cell assay and, finally, inhibition of HIV-1 replication.

Moreover, the present invention extends to a method of utilizing a carrier of the present invention conjugated to a peptide comprising an amino acid sequence as set forth in SEQ ID NO:8, and biologically and pharmaceutically acceptable salts thereof, to treat a viral infection in a mammal in need of such treatment. Such a method comprises administering to a mammal a therapeutically effective amount of a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, and the therapeutic agent comprises a biotinylated peptide comprising an amino acid sequence as set forth in SEQ ID NO:8.

In particular, methods of the present invention stated above can be used to treat retroviral infections such as AIDS, in humans.

Moreover, the invention extends to a carrier for in vivo delivery of a therapeutic agent, comprising a polymer which has a branched or linear structure. For purposes of this application, the term "polymer" encompasses both homopolymers and copolymers. Preferably, the polymer is a water soluble polymer.

Examples of water soluble polymers which have applications in the present invention include, but are not limited to, polyethylene glycol, carboxymethylcellulose, dextran, polyvinyl alcohol, polyvinyl pyrrolidone, poly-1,3-dioxolane, poly-1,3,6-trioxane, polyaminoacids (homopolymers), polypropylene glycol, copolymers of ethylene glycol/propylene glycol, ethylenelmaleic anhydride copolymer, polyaminoacids, copolymer of polyethylene glycol and an amino acid, polypropylene oxide/ethylene oxide copolymers, or polyethylene glycol/thiomalic acid copolymers. In a preferred embodiment, the polymer comprises a copolymer of polyethylene glycol and lysine.

Moreover, a thiol compound can be conjugated to the polymer of the carrier, or conjugated to at least one functional group attached to the polymer which is available for reaction with the thiol compound, provided the thiol group of the thiol compound is available to form a disulfide bond with a thiol group of the therapeutic agent.

Numerous functional groups can be attached to a polymer of a carrier of the present invention and used to conjugate a thiol compound thereto. Moreover, more than one type of functional group can be concurrently attached to the polymer, and available to conjugate a thiol compound to the polymer. Examples of functional groups having applications in this embodiment of the present invention include, but are not limited to, ketones, esters, carboxylic acids, aldehydes, alcohols, thiols, or amines. In a preferred embodiment, the polyethylene glycol/lysine copolymer has a carboxylic acid group attached thereto, and available for reaction. Hence, more than one molecule of therapeutic agent can be conjugated to a carrier of the present invention, and delivered to a target cell or tissue.

A polymer of a carrier of the present invention can have any molecular weight. In an embodiment of the invention, the polymer has a molecular weight range of about 1,000 to about 1,000,000 Daltons, and preferably a molecular weight range of about 20,000 to 200,000 Daltons. In a preferred embodiment, the polymer has a molecular weight of about 27,000 Daltons.

The present invention further extends to a carrier for in vivo delivery of a therapeutic agent comprising a thiol group, wherein the carrier comprises a polymer, and at least one thiol compound conjugated to the polymer at an interval so that the thiol group of the at least one thiol compound and a thiol group of a therapeutic agent can form a disulfide bond. As used herein, the term "interval" indicates a distance between thiol compounds conjugated to the polymer of a carrier of the present invention. In an embodiment, the interval between thiol compounds conjugated to the polymer is about 100 to about 10,000 Daltons. In a preferred embodiment, the interval between conjugation of thiol compounds to a polymer of the carrier is about 300 to about 3,000 Daltons.

Furthermore, the present invention extends to a carrier comprising a polymer with functional groups attached thereto, wherein the functional groups are available for conjugation to a thiol compound, and are attached to the polymer at an interval. In an embodiment, the interval between functional groups attached to the polymer is about 100 to about 10,000 Daltons. In a preferred embodiment, the interval between functional groups attached to a polymer of the carrier is about 300 to about 3,000 Daltons.

Moreover, examples of thiol compounds having applications in a carrier of the present invention include, but are not limited to, cysteamine, 1-amino-2-methyl-2-propanethiol, or 1-amino-2-propanethiol, to name only a few.

In addition, the present invention extends to a carrier for in vivo delivery of a therapeutic agent having a thiol group, wherein the carrier further comprises a cell uptake promoter conjugated to the polymer. The cell uptake promoter enhances the ability of the carrier with the therapeutic agent conjugated thereto, to cross a cell membrane and enter the cell's cytosol.

Numerous cell uptake promoters are known, and have applications in embodiments of the present invention. An example of a cell uptake promoter having applications therein is biotin. Hence, conjugation of biotin to a polymer of a carrier of the present invention enhances the ability of the carrier, and the therapeutic agent attached thereto via a disulfide bond, to cross a cell membrane and enter a cell's cytosol. Once inside the cell, the disulfide bond between the therapeutic agent and the carrier is reduced, and the therapeutic agent is released to act upon its target.

Moreover, it has been discovered that the cell uptake promoter need not be conjugated only to the polymer in order to be effective. Rather, the cell uptake promoter can also be conjugated to the therapeutic agent, and still enhance the ability of the carrier and the therapeutic agent to cross a cell membrane.

The present invention further extends to methods of making a carrier for in vivo delivery of a therapeutic agent comprising a thiol group, wherein the carrier comprises a polymer and at least one thiol compound conjugated to the polymer, such that the thiol group of the thiol compound and the thiol group of the therapeutic agent form a disulfide bond. One such method disclosed herein comprises the steps of:

a) reacting a thiol compound with a disulfide compound to form a first intermediate wherein the thiol group of the thiol compound and a sulfur atom of the disulfide bond of the disulfide compound form a disulfide bond; and b) reacting the first intermediate with a polymer to form the carrier, wherein the first intermediate is conjugated to the polymer, so that the sulfur atom of the thiol compound of the carrier and the thiol group of the therapeutic agent can form a disulfide bond.

Any disulfide compound can be used in step (a) of the method recited above. Preferably, the disulfide compound is symmetric. In an embodiment of the present invention, the disulfide compound is 2,2'-dithiodipyridine.

Another method of making a carrier for in vivo delivery of a therapeutic agent comprising a thiol group, as set forth herein, comprises the steps of:
  a) reacting a first thiol compound with a second thiol compound to form a first intermediate comprising a disulfide bond;
  b) reacting the first intermediate with a polymer to form a second intermediate, wherein the first intermediate is conjugated to the polymer;
  c) reducing the disulfide bond to form a third intermediate comprising the polymer and the first thiol compound conjugated to the polymer so that the thiol group of the first thiol compound is available for reaction; and
  d) reacting the third intermediate with a disulfide compound to form the carrier, wherein the thiol group of the first thiol compound and a sulfur atom of the disulfide bond of the disulfide compound form a disulfide bond.

Under appropriate conditions, the sulfur atom of the first thiol compound and the thiol group of the therapeutic agent can form a disulfide bond.

In an embodiment of the present invention, the first thiol compound and the second thiol compound are the same compound.

Numerous thiol compounds have applications in methods of the present invention. Examples include cysteamine, t-amino-2-methyl-2-propanethiol, and 1-amino-2-propanethiol, to name only a few.

Moreover, any disulfide compound can be used in step (d) of this method. Preferably, the disulfide compound is symmetric. In an embodiment of the present invention, the disulfide compound is 2,2'-dithiodipyridine.

In an embodiment of the present invention, a therapeutic agent comprising a thiol group is a Tat-inhibitory peptide derivative, and comprises a biotinylated peptide of the formula I:

R-Arg-Lys-Lys-Arg-Arg-Gln-Arg-Arg-Arg-X-(biotin)-Cys-NH$_2$ (SEQ ID NO:1)

wherein R is the residue of a carboxylic acid or an acetyl group, and X is a Cys or Lys residue, and analogs thereof, and the biologically and pharmaceutically acceptable salts thereof, and all stereo, optical and geometrical isomers thereof where such isomers exist, as well as the pharmaceutically acceptable salts and solvates thereof. Examples of analogs of such a therapeutic agent include, but are not limited to:

N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO:3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO:5)
N-acetyl-Gln-Lys-Lys-Arg-Arg-Gln-Arg-Arg-Arg-D-Lys-(biotin)-Cys-NH$_2$ (SEQ ID NO:6)
N-acetyl-Arg-Lys-Lys-Arg-Arg-Pro-Arg-Arg-Arg-Cys-(biotin)-Cys-NH$_2$ (SEQ ID NO:7).

In another embodiment of the present invention, a therapeutic agent comprising a thiol group is a Tat-inhibitory peptide derivative comprising an amino acid sequence of SEQ ID NO:8:

N-acetyl-DCys-DLys-(biotin)-DArg-DArg-DArg-DGln-DArg-DArg-DLys-DLys-DArg-NH$_2$ (SEQ ID NO:8)

analogs or derivatives thereof, as well as all pharmaceutically acceptable salts thereof.

The production of such agents can readily be accomplished with presently known method of producing peptide including, but not limited to solid phase synthesis of peptides. Moreover, it is also readily apparent to one skilled in the art on methods of biotinylating such peptides.

The present invention further extends to methods of making a carrier for in vivo delivery of a therapeutic agent, as set forth above, wherein the polymer has a branched or linear structure. Preferably, the polymer is a water soluble polymer. Examples of water soluble polymers having applications herein include polyethylene glycol, carboxymethylcellulose, dextran, polyvinyl alcohol, polyvinyl pyrrolidone, poly-1,3-dioxolane, poly-1,3,6-trioxane, polyaminoacids (homopolymers), polypropylene glycol, copolymers of ethylene glycol/propylene glycol, ethylene/maleic anhydride copolymer, polyaminoacids, copolymer of polyethylene glycol and an amino acid, polypropylene oxide/ethylene oxide copolymers, or polyethylene glycol/thiomalic acid copolymers.

Moreover, a polymer used in methods of the present invention can have any molecular weight. In an embodiment of the present invention, a polymer has a molecular weight range of about 1,000 to about 1,000,000 Daltons, and preferably a molecular weight range of about 20,000 to 200,000 Daltons. In a preferred embodiment, the polymer has a molecular weight of about 27,000 Daltons. The present invention also extends to methods of making a carrier for in vivo delivery of a therapeutic agent comprising a thiol group, comprising a polymer and at least one thiol compound conjugated to the polymer at an interval. In an embodiment of the invention, the interval between thiol compounds conjugated to the polymer is about 100 to about 10,000 Daltons, and preferably about 300 to about 3,000 Daltons.

The present invention further extends to methods for making carriers for in vivo delivery of a therapeutic agent comprising a thiol group, further comprising the step of conjugating a cell uptake promoter to the polymer prior to reacting the polymer with an intermediate. The cell uptake promoter enhances the ability of the carrier bound to the therapeutic agent to cross a cell membrane and enter the cell's cytosol.

Numerous cell uptake promoters are known, and have applications in the present invention. An example of a cell uptake promoter is biotin. Hence, conjugating biotin to a polymer of a carrier of the present invention enhances the ability of the carrier and the therapeutic agent conjugated thereto, to cross a cell membrane and enter a cell's cytosol. As explained above, once the carrier crosses the cell membrane and enters the cytosol, the disulfide bond is reduced, and agent is released to act on its target.

Moreover, it has been discovered that the cell uptake promoter need not be attached only to the polymer. Rather, the cell uptake promoter can also be conjugated to the therapeutic agent, and still enhance the ability of the carrier and the therapeutic agent to cross a cell membrane.

The present invention further extends to a method of making a carrier for in vivo delivery of a therapeutic agent comprising a thiol group, wherein the carrier comprises a polymer comprising at least one functional group attached thereto, and a thiol compound conjugated to the at least one functional group, such that the thiol group of the thiol compound and the thiol group of the therapeutic agent form a disulfide bond. An example of a method for making such a carrier comprises the steps of:

a) reacting a thiol compound with a disulfide compound to form a first intermediate wherein the thiol group of the thiol compound and a sulfur atom of the disulfide bond of the disulfide compound form a disulfide bond; and b) reacting the first intermediate with a polymer comprising at least one functional group attached thereto to form the carrier, wherein the first intermediate is conjugated to the functional group so that the sulfur atom of the thiol compound and the thiol group of the therapeutic agent can form a disulfide bond under appropriate conditions.

Furthermore, the present invention extends to a method of making a carrier for in vivo delivery of a therapeutic agent comprising a thiol group, as set forth herein, comprising the steps of:

a) reacting a first thiol compound with a second thiol compound to form a first intermediate, wherein the thiol group of the first thiol compound and the thiol group of the second thiol compound form a disulfide bond;

b) reacting the first intermediate with a polymer comprising at least one functional group attached thereto to form a second intermediate, wherein the first intermediate is conjugated to the at least one functional group;

c) reducing the disulfide bond of the second intermediate to form a third intermediate comprising the polymer with at least one functional group and the first thiol compound conjugated to the functional group, so that the thiol group of the first thiol compound is available for reaction;

d) reacting the third intermediate with a disulfide compound to form the carrier, wherein the thiol group of the first thiol compound and a sulfur atom of the disulfide bond of the disulfide compound form a disulfide bond. Hence, under appropriate conditions, the disulfide bond of the carrier can be reduced, and the sulfur atom of the first thiol compound and the thiol, group of the therapeutic agent can form a disulfide bond.

In an embodiment of the present invention, the first thiol compound and the second thiol compound can be the same compound.

The present invention extends to methods of making a carrier of the present invention, as set forth above, wherein the at least one functional group attached to a polymer used in methods of the present invention comprises a ketone, an ester, a carboxylic acid, an aldehyde, an alcohol, a thiol, or an amine, to name only a few.

Moreover, the present invention extends to methods of making a carrier of the present invention as described above, wherein the at least one functional group is attached to the polymer of a carrier of the present invention at an interval. In an embodiment of the invention, the interval between functional groups attached to the polymer is about 100 to about 10,000 Daltons, and preferably about 300 to about 3,000 Daltons.

As stated above, a therapeutic agent conjugated to a carrier of the present invention comprises at least one thiol group. In an example, a therapeutic agent conjugated to a carrier of the present invention comprises a Tat inhibitory peptide derivative of the formula I:

R-Arg-Lys-Lys-Arg-Arg-Gln-Arg-Arg-Arg-X-(biotin)-Cys-NH$_2$ (SEQ ID NO: 1)

wherein R is the residue of a carboxylic acid or an acetyl group, and X is a Cys or Lys residue, and analogs thereof, and the biologically and pharmaceutically acceptable salts thereof, along with all stereo, optical and geometrical isomers thereof, where such isomers exist, and pharmaceutically acceptable salts and solvates thereof.

Moreover, examples of analogs of such a therapeutic agent having applications in the present invention include, but are not limited to:

N-acetyl-Arg-Lys-Lys-Arg-Arg-Gln-Arg-Arg-Arg-Cys-(biotin)-Cys-NH$_2$ (SEQ ID NO:2)

N-acetyl-Arg-Lys-Lys-Arg-Arg-Gln-Arg-Arg-Arg-Lys-(biotin)-Cys-NH$_2$ (SEQ ID NO:3)

N-acetyl-Arg-Lys-Lys-Arg-Arg-Gln-Arg-Arg-Arg-D-Cys-(biotin)-Cys-NH$_2$ (SEQ ID NO:4)

N-acetyl-Arg-Lys-Lys-Arg-Arg-Gln-Arg-Arg-Arg-D-Lys-(biotin)-Cys-NH$_2$ (SEQ ID NO:5)

N-acetyl-Gln-Lys-Lys-Arg-Arg-Gln-Arg-Arg-Arg-D-Lys-(biotin)-Cys-NH$_2$ (SEQ ID NO:6)

N-acetyl-Arg-Lys-Lys-Arg-Arg-Pro-Arg-Arg-Arg-Cys-(biotin)-Cys-NH$_2$ (SEQ ID NO:7), to name only a few.

In another embodiment, a therapeutic agent comprising a thiol group and conjugated to a carrier of the present invention, comprises an amino acid sequence as set forth in SEQ ID NO:8:

N-acetyl-DCys-DLys-(biotin)-DArg-DArg-DArg-DGln-DArg-DArg-DLys-DLys-DArg-NH$_2$ (SEQ ID NO:8).

or analogs or derivatives thereof, and pharmaceutically acceptable salts thereof.

Applicants have also discovered that the release rate of a therapeutic agent from a carrier of the present invention can be modulated, depending on the steric hindrance of the thiol compound of the carrier. In particular, Applicants have discovered that the greater the steric hindrance of the thiol compound, the slower the release rate of the therapeutic agent from the carrier. Hence, the present invention extends to a carrier for in vivo delivery of a therapeutic agent comprising a thiol group, wherein the carrier comprises a polymer and at least one thiol compound comprising at least one functional group, conjugated to the polymer, such that the thiol group of the thiol compound and the thiol group of the therapeutic agent can form a disulfide bond, and the rate at which the disulfide bond is reduced in an appropriate physiological environment is dependent on the size of the at least one functional group attached to the thiol compound.

Moreover, the present invention extends to methods of making a carrier of the present invention as described above, wherein the at least one functional group is attached to the polymer of a carrier of the present invention at an interval. In an embodiment of the invention, the interval between functional groups attached to the polymer is about 100 to about 10,000 Daltons, and preferably about 300 to about 3,000 Daltons.

The present invention further extends to another embodiment wherein the release rate of a therapeutic agent from a carrier of the present invention can be modulated depending on the steric hindrance of the thiol compound of the carrier. In particular, disclosed herein is a carrier for in vivo delivery of a therapeutic agent comprising a thiol group, wherein the carrier comprises a polymer and at least one thiol compound comprising at least one functional group, and a polymer comprising at least one functional group available for reaction, so that the thiol compound is conjugated to the at least one functional group attached to the polymer, and the thiol group of the thiol compound and the thiol group of the therapeutic agent can form a disulfide bond. The rate of reduction of the disulfide bond inking the therapeutic agent to the carrier is dependent on the size of the at least one functional group attached to the thiol compound.

Accordingly, it is a principal object of the present invention to provide a carrier for in vivo delivery of a therapeutic agent which can be conjugated to a carrier via a disulfide bond.

It is a further object of the invention to provide a carrier for in vivo delivery of a therapeutic agent, wherein the therapeutic agent is conjugated to the carrier via a biodegradable disulfide bond which is difficult to reduce in extracellular fluids in vivo.

It is a further object of the present invention to provide a carrier for in vivo delivery of a therapeutic agent which will remain substantially conjugated to the carrier until the carrier crosses a cell membrane. Once inside the cell, the cytosolic environment reduces the disulfide bond conjugating the therapeutic agent to the carrier, and the therapeutic agent is released to act on its target.

It is a further object of the present invention to provide a carrier for in viva delivery of a therapeutic agent which increases the bioavailability of the therapeutic agent so that the rate of repeated parenteral administration of the therapeutic agent can be minimized.

It is yet another object of the present invention to provide methods of modulating the release of a therapeutic agent in vivo wherein the release rate of the therapeutic agent from the carrier is dependent upon three dimensional configuration of a thiol compound used in methods of making carriers of the present invention.

Yet still another object of the present invention is to provide a carrier for in vivo delivery of a therapeutic agent comprising a thiol group which has a structure that can reduce the rate at which the therapeutic agent is released from the carrier. This object can be used to cause the timed release of the therapeutic agent in vivo.

It is yet another object of the present invention to provide a carrier for in vivo delivery of a therapeutic agent comprising a thiol group, wherein the therapeutic agent is a Tat-inhibitory polypeptide derivative, analogs thereof, or biologically and pharmaceutically acceptable salts thereof.

It is yet another object of the present invention to provide a carrier for in vivo delivery of a therapeutic agent comprising a thiol group, wherein the therapeutic agent is a Tat-inhibitory peptide derivative, and administration of a carrier of the present invention conjugated to a Tat-inhibitory peptide derivative disclosed herein can be used to treat a mammal suffering from a retroviral infection, such as AIDS.

Other objects and advantages will become apparent to those skilled in the art from a review of the ensuing description which proceeds with reference to the following illustrative drawings.

DETAILED DESCRIPTION OF THE INVENTION

Figure 1:
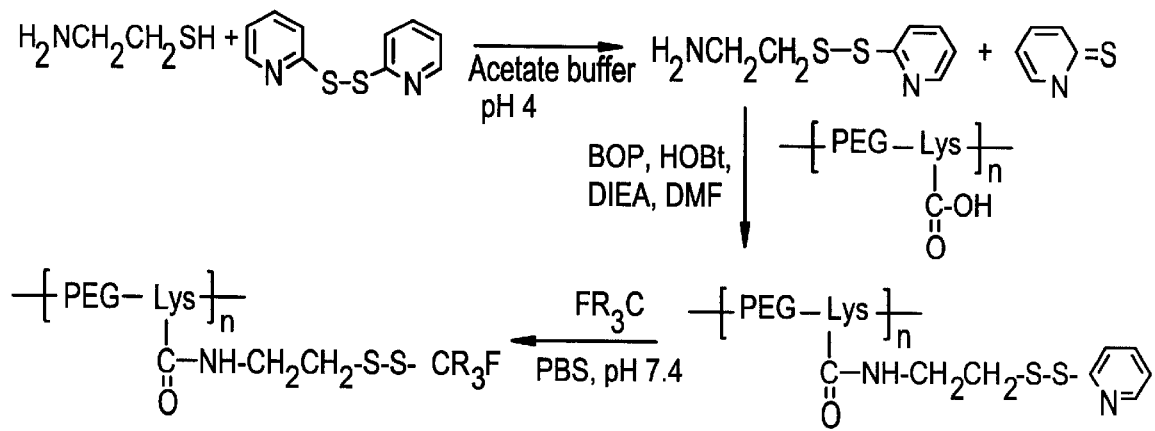
FIG. 1 is a schematical drawing of Scheme I of producing a carrier for in vivo delivery of a therapeutic agent comprising a thiol group.
Figure 2:
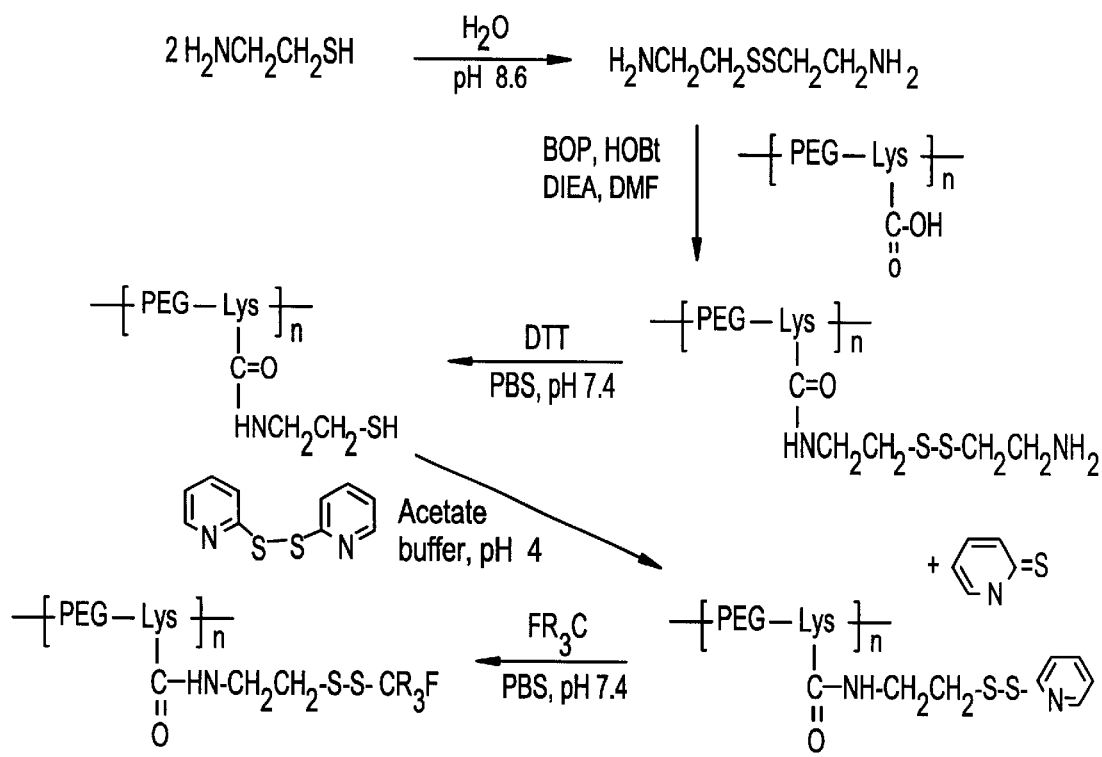
FIG. 2 is a schematical drawing of Scheme II for producing a carrier for in vivo delivery of a therapeutic agent comprising a thiol group.

The present invention is based on Applicants' discovery that unexpectedly, a biodegradable disulfide bond can be used to conjugate a therapeutic agent to a carrier for in vivo delivery of the therapeutic agent, wherein the carrier comprises a polymer and a thiol compound conjugated to the polymer, so that the thiol group of the thiol compound and the thiol group of the therapeutic agent can form a disulfide bond. Extracellular media in vivo does not provide an appropriate environment for appreciably reducing a disulfide bond. Hence, a disulfide bond conjugating the therapeutic agent to the polymer remains relatively stable during the circulation of the carrier throughout the intercellular matrix of the body. In contrast, cytosol of a cell provides the appropriate environment for reducing a disulfide bond, particularly since the reduced form of glutathione, a naturally occurring reducing agent, is found predominantly in the cytosol. Once the carrier crosses a cell membrane and enters the cytosol, the disulfide bond conjugating the therapeutic agent to the carrier is reduced, and the therapeutic agent is released to act upon its target in the cell. Consequently, a substantial portion of a therapeutic agent conjugated to a carrier of the present invention and administered to a subject, is delivered to target cells, and then released.

The term "about" as used herein to describe molecular weights indicates that in preparations of polymers, some molecules will weigh more, some less, than the stated molecular weight.

The term "steric hindrance" as used herein describes an effect on relative reaction rates caused by the space-filling properties of those parts of a molecule attached at or near the reacting site.

The term "bioavailability" as used herein refers to the ability of a therapeutic agent to reach its target cell or to reach its molecular target inside a cell.

The term "polymer" as used herein encompasses both homopolymers and copolymers.

As used herein, the term "interval" indicates a distance between thiol compounds conjugated to a polymer of a carrier of the present invention, or the distance between functional groups attached to a polymer of a carrier of the present invention.

Moreover, as used herein, the term "therapeutically effective" is used herein to mean an amount sufficient to prevent, and preferably reduce by at least about 30 percent, more preferably by at least 50 percent, most preferably by at least 90 percent, transactivation of viral TAR RNA by Tat protein.

The polymer of a carrier of the present invention can have either a branched or linear structure. Preferably, the polymer is a water soluble polymer.

Examples of water soluble polymers which have applications in the present invention include, but are not limited to, polyethylene glycol, carboxymethylcellulose, dextran, polyvinyl alcohol, polyvinyl pyrrolidone, poly-1,3-dioxolane, poly-1,3,6-trioxane, polyaminoacids (homopolymers), polypropylene glycol, copolymers of ethylene glycol/propylene glycol, ethylene/maleic anhydride copolymer, polyaminoacids, copolymer of polyethylene glycol and an amino acid, polypropylene oxide/ethylene oxide copolymers, or polyethylene glycol/thiomalic acid copolymers. In a preferred embodiment, the polymer is a copolymer of polyethylene glycol and lysine. Methods of making such a copolymer are set forth in Nathan, A., Zalipsky, S., Ertel, S. I., Agathos, S. N., Yarmush, M. L. And Kohn, J. (1993) *Copolymers of lysine and polyethylene glycol: A new family of functionalized drug carriers*. Bioconj. Chem. 4:54–62 which is incorporated by reference herein in its entirety.

A polymer of a carrier of the present invention can have any molecular weight. In one embodiment of the present invention, the polymer has a molecular weight range of about 1,000 to about 1,000,000 Daltons, and preferably a molecular weight range of about 20,000 to 200,000 Daltons. More preferably, the polymer of a carrier of the present invention has a molecular weight of about 27,000 D.

The present invention further extends to a carrier for in vivo delivery of a therapeutic agent comprising a thiol group, wherein the carrier comprises a polymer, and at least one thiol compound conjugated to the polymer at an interval, such that the thiol group of the thiol compound and the thiol group of the therapeutic agent form a disulfide bond.

In an embodiment, the interval between thiol compounds conjugated to a polymer of a carrier of the present invention is about 100 to about 10,000 Daltons. In a preferred embodiment, the interval between thiol compounds is about 300 to about 3,000 Daltons. Hence, more than one molecule of therapeutic agent can be conjugated to a carrier of the present invention, and delivered to its target tissue or cells.

Moreover, the present invention further extends to a carrier for in vivo delivery of a therapeutic agent comprising a thiol group, wherein the carrier comprises a polymer comprising at least one functional group attached thereto and available for reaction, and a thiol compound conjugated to the at least one functional group, so that the thiol group of the thiol compound and the thiol group of the therapeutic agent form a disulfide bond.

Attachment of functional groups to a polymer can be accomplished with standard organic chemistry techniques. Since numerous water soluble polymers and numerous functional groups have applications in the present invention, the chemical synthetic route used to attach the at least one functional group are dependent on the polymer, and the functional group one would like to attach thereto. In a preferred embodiment of the present invention, the polymer comprises a copolymer of polyethylene glycol and lysine, which inherently has a carboxylic acid functional group attached to lysine and available for reaction.

Moreover, in an embodiment of the present invention, the functional groups are attached to the polymer at an interval of about 100 to about 10,000 Daltons. In a preferred embodiment, the interval between functional groups is about 300 to about 3,000 Daltons.

Examples of functional groups which can be attached to a polymer of a carrier of the present invention include ketones, esters, carboxylic acids, aldehydes, alcohols, thiols, or amines, to name only a few. In a preferred embodiment of the present invention, the functional group is a carboxylic acid. Moreover, more than one type of functional group can be concurrently attached to a polymer of a carrier of the present invention.

Furthermore, examples of thiol compounds having applications in a carrier of the present invention include, but are not limited to, cysteamine, I-amino-2-methyl-2-propanethiol, or 1-amino-2-propanethiol, to name only a few.

In addition, the present invention extends to a carrier for in vivo delivery of a therapeutic agent having a thiol group, wherein the carrier comprises a polymer, a cell uptake promoter conjugated to the polymer, and at least one thiol compound conjugated to the polymer, such that the thiol group of the at least one thiol compound can form a disulfide bond with the thiol group of therapeutic agent. The cell uptake promoter enhances the ability of a carrier of the present invention conjugated to a therapeutic agent via a disulfide bond to cross a cell membrane and enter the cell's cytosol.

Numerous cell uptake promoters are known, and have applications in the present invention. An example of a cell uptake promoter having applications in the present invention is biotin. Moreover, methods of biotinylating a chemical compound, such as a carrier of the present invention, are known to the skilled artisan, and are not discussed in detail here.

Moreover, as set forth in examples described below, a cell uptake promoter can also be attached directly to the therapeutic agent comprising a thiol group, and still enhance the ability of the carrier and the therapeutic agent to cross a cell membrane.

In addition, an example of a therapeutic agent comprising a thiol group which can be conjugated to a carrier of the present invention, comprises a Tat-inhibitory binding peptide comprising a sequence of formula I:

R-Arg-Lys-Lys-Arg-Arg-Gln-Arg-Arg-Arg-X-(biotin)-Cys-$NH_2$ (SEQ ID NO: 1)

wherein R is the residue of a carboxylic acid or an acetyl group, and X is a Cys or Lys residue, and analogs thereof, and the biologically and pharmaceutically acceptable salts thereof, and stereo, optical and geometrical isomers thereof, where such isomers exist, along with pharmaceutically acceptable salts and solvates thereof. Such agents are useful in the treatment of viral infections such as HIV-1 infection in mammals, by virtue of their ability to block the interaction of Tat protein with TAR RNA, thereby interfering with the transactivation step in the replication cycle of HIV-1. The rationale for this approach is that such peptides compete with the full length Tat protein for binding to TAR RNA, thereby preventing the required interactions between other domains in Tat protein and the nascent transcription apparatus.

In another embodiment, the therapeutic agent conjugated to a carrier of the present invention is a Tat-inhibitory peptide comprising an amino acid sequence of SEQ ID NO: 8:
N-acetyl-DCys-DLys-(biotin)-DArg-DArg-DArg-DGln-DArg-DArg-DLys-DLys-DArg-NH$_2$ (SEQ ID NO:8)
along with pharmaceutically acceptable salts thereof, and analogs and derivatives thereof.

Indeed, cell culture experiments using promoter elements of the HIV-1 LTR linked to the reporter CAT gene demonstrate that therapeutic agents comprising a thiol group, as described above, and containing the 9-amino acid basic domain of Tat protein block the transactivation process.

Moreover, there is convincing evidence from a HLCE-D36 cell assay that a representative peptide of formula I, Tat10-biotin, specifically blocks Tat protein-mediated expression of CAT protein (please see Choudhury, I., Wang, J., Rabson, A. B., Stein, S., Pooyan, S., Stein, S. and Leibowitz, M. J. (1998) Inhibition of HIV-1 replication by a Tat RNA binding domain peptide analog. *J. Acqu. Immune Def. Syndr. & Human Retrovirol.*, 17, 104–111, which is incorporated by reference in its entirety). Although the mechanism whereby Tat protein induces protein expression from the HIV LTR is generally believed to be due to an effect on transcriptional elongation, it is possible that there are also post-transcriptional effects of Tat protein. Thus, whether Tat10-biotin competes with Tat protein only at the transcriptional elongation step remains to be determined. Regardless, Applicants are under no obligation to explain such a mechanism, and are not to be bound by postulates of the mechanism set forth above.

The instant invention thus provides a method of treating a retroviral infection in a mammal in need of such treatment. Such a method comprises administering to a mammal a therapeutically effective amount of a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, wherein the therapeutic compound comprising a thiol group comprises a Tat-inhibitory binding peptide derivative. For example, a Tat-inhibitory binding derivative having applications in this method comprises a biotinylated peptide of the formula I:
R-Arg-Lys-Lys-Arg-Arg-Gln-Arg-Arg-Arg-X-(biotin)-Cys-NH$_2$ (SEQ ID NO:1)
wherein R is the residue of a carboxylic acid or an acetyl group, and X is a Cys or Lys residue, and analogs thereof, and the biologically and pharmaceutically acceptable salts thereof, or stereo, optical and geometrical isomers thereof, where such isomers exist, and pharmaceutically acceptable salts and solvates thereof.

Examples of Tat inhibitory binding derivatives of formula I include, but are not limited to:

N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO:3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO:5)
N-acetyl-Gln-Lys-Lys-Arg-Arg-Gln-Arg-Arg-Arg-D-Lys-(biotin)-Cys-NH$_2$ (SEQ ID NO:6),
or
N-acetyl-Arg-Lys-Lys-Arg-Arg-Pro-Arg-Arg-Arg-Cys-(biotin)-Cys-NH$_2$ (SEQ ID NO:7)
or analogs or derivatives thereof, or pharmaceutically acceptable salts thereof.

In another example, a Tat-inhibitory peptide derivative which can be conjugated to a carrier of the present invention comprises an amino acid sequence of SEQ ID NO:8
N-acetyl-DCys-DLys-(biotin)-DArg-DArg-DArg-DGln-DArg-DArg-DLys-DLys-DArg-NH$_2$ (SEQ ID NO:8)
or analogs or derivatives thereof, or pharmaceutically acceptable salts thereof.

As explained above, numerous methods are readily available to synthesize such peptide derivatives. For example, they can be produced via recombinant expression of a specially engineered DNA molecule which encodes such a peptide. Moreover, such peptides can be synthesized using readily available solid phase synthesis techniques. After synthesis of such peptides, they can be readily biotinylated using presently known methods of biotinylation.

As explained above, Tat-inhibitory peptide derivatives disclosed herein can be utilized as Tat protein RNA-binding domain mimics to treat the HIV-1 infection, and the resultant AIDS. The mammal under treatment can be a human, monkey, cat or the like, with the treatment of humans being particularly preferred. A carrier for in vivo delivery, wherein the therapeutic agent comprises a Tat antagonist should also be useful for ameliorating the pathogenic effects of Tat protein on host cells due to interactions with TAR-like elements on cellular transcripts. Recent studies on peptide analogs of the core domain sequence of Tat protein, which is believed to interact with host cell factors rather than with virally encoded RNA, have lead to the same suggestion for a new class of therapeutic agents for AIDS based on inhibition of the transactivation step in the HIV-1 replication cycle. Hence, coupling such agents to a carrier of the present invention substantially reduces degradation and renal clearance of the agents in vivo prior to their interaction with the target tissue, and increases the bioavailability of such therapeutic agents to their intended target tissues and cells.

The polypeptides of formula I and their analogs, along with the amino acid sequence of SEQ ID NO:8, analogs or derivatives thereof, can be synthesized by conventional solution methods, or by solid phase synthetic techniques known in the art.

Throughout the specification and appended claims, the polypeptide of formula I, and its analogs and derivatives, and salts, encompass all stereo, optical and geometrical isomers thereof where such isomers exist, as well as the pharmaceutically acceptable salts and solvates thereof. Where appropriate, the polypeptide or its analogs can be utilized as its corresponding amide form. The amino acid residues described herein are preferred to be in the "L" isomeric form. However, residues in the "ID" isomeric form can be substituted for any L-amino acid residue, as long as the desired functional property is retained by the polypeptide.

The R group of the peptides of formula I can be any residue of an alkyl, alkenyl or aryl carboxylic acid, i.e., acetic, propionic, butyric, valeric, allylic, benzoic and the like being suitable. Particularly preferred for use in the present invention is the acetyl derivative of the peptides of formula I.

The term "biologically and pharmaceutically acceptable salts" is intended to include any such salt derived from an inorganic or organic acid which is tolerated by the mammalian system. These salts include, but are not limited to, acetate, adipate, alginate, citrate, aspartate, benzoate, benzenesulfonate, bisulfate, hexanoate, succinate, fumarate, hydrochloride, hydrobromide, lactate, maleate, phosphate, sulfate, methanesulfonate, oxalate, propionate, tosylate, and mesylate. Examples of acids which can be used to form such salts include such inorganic acids as hydrochloric acid, sulfuric acid and phosphoric acid, and such organic acids such as oxalic acid, maleic acid, succinic acid and citric acid.

The nomenclature used to define the polypeptides is that specified by Schroder & Lubke, "The Peptides", Academic Press (1965), wherein in accordance with conventional representation the amino group at the N-terminal appears to the left and the carboxyl group at the C-terminal to the right. $NH_2$ refers to the amide group present at the carboxy terminus when written at the right of a polypeptide sequence.

Accordingly, polypeptide analogs displaying substantially equivalent activity to the polypeptide of formula I are likewise contemplated for use in the present invention. These modifications can be obtained through peptide synthesis utilizing the appropriate starting material.

In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

An amino acid in the polypeptide of this invention can be changed in a non-conservative manner (i.e., by changing an amino acid belonging to a grouping of amino acids having a particular size or characteristic to an amino acid belonging to another grouping) or in a conservative manner (i.e., by changing an amino acid belonging to a grouping of amino acids having a particular size or characteristic to an amino acid belonging to the same grouping). Such a conservative change generally leads to less change in the structure and function of the resulting polypeptide. The present invention should be considered to include analogs whose sequences contain conservative changes which do not significantly alter the activity or binding characteristics of the resulting polypeptide.

The following is one example of various groupings of amino acids:
Amino Acids with Nonpolar R Groups
Alanine
Valine
Leucine
Isoleucine
Proline
Phenylalanine
Tryptophan
Methionine
Amino Acids with Uncharged Polar R Groups
Glycine
Serine
Threonine
Cysteine
Tyrosine
Asparagine
Glutamine
Amino Acids with Charged Polar R Groups (Negatively Charged at pH 6.0)
Aspartic acid
Glutamic acid
Basic Amino Acids (Positively Charged at pH 6.0)
Lysine
Arginine
Histidine (at pH 6.0)

Another grouping may be those amino acids with aromatic groups:
Phenylalanine
Tryptophan
Tyrosine Another grouping may be according to molecular weight (i.e., size of R groups):

| Glycine | 75 |
|---|---|
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |

| | |
|---|---|
| Phenylalanine | 165 |
| Arginine | 174 |
| Tyrosine | 181 |
| Tryptophan | 204 |

Particularly preferred substitutions are:
Gln for Arg or Lys; and
His for Lys or Arg.

Amino acid substitutions may also be introduced to substitute an amino acid with a particularly preferable property. For example, a Cys may be introduced a potential site for disulfide bridges with another Cys, or with a carrier of the present invention. A His may be introduced as a particularly "catalytic" site (i.e., His can act as an acid or base and is the most common amino acid in biochemical catalysis). Pro may be introduced because of its particularly planar structure, which induces βturns in the polypeptide's structure. Alternately, D-amino acids can be substituted for the L-amino acids at one or more positions.

Representative analogs of the polypeptide of formula I thus include:

N-acetyl-Arg-Lys-Lys-Arg-Arg-Gln-Arg-Arg-Arg-Cys-(biotin)-Cys-$NH_2$ (SEQ ID NO:2)

N-acetyl-Arg-Lys-Lys-Arg-Arg-Gln-Arg-Arg-Arg-Lys-(biotin)-Cys-$NH_2$ (SEQ ID NO:3)

N-acetyl-Arg-Lys-Lys-Arg-Arg-Gln-Arg-Arg-Arg-D-Cys-(biotin)-Cys-$NH_2$ (SEQ ID NO:4)

N-acetyl-Arg-Lys-Lys-Arg-Arg-Gln-Arg-Arg-Arg-D-Lys-(biotin)-Cys-$NH_2$ (SEQ ID NO:5)

N-acetyl-Gln-Lys-Lys-Arg-Arg-Gln-Arg-Arg-Arg-D-Lys-(biotin)-Cys-$NH_2$ (SEQ ID NO:6)

N-acetyl-Arg-Lys-Lys-Arg-Arg-Pro-Arg-Arg-Arg-Cys-(biotin)-Cys-$NH_2$ (SEQ ID NO:7)

Also disclosed herein are methods of making a carrier for in vivo delivery of a therapeutic agent comprising a thiol group, wherein the carrier comprises a polymer, and at least one thiol compound conjugated to the polymer, such that the thiol group of the at least one thiol compound and the thiol group of the therapeutic agent form a disulfide bond.

One such method disclosed herein comprises the steps of:

a) reacting at least one thiol compound with a disulfide compound to form a first intermediate wherein the thiol group of the at least one thiol compound and a sulfur atom of the disulfide bond of the disulfide compound form a disulfide bond; and b) reacting the first intermediate with the polymer to form the carrier comprising the first intermediate conjugated to the polymer.

Once the carrier has been produced, it can be reacted with a therapeutic agent comprising a thiol group, so that its disulfide bond is reduced, and the sulfur atom of the at least one thiol compound of the carrier, and the thiol group of the therapeutic agent can form a disulfide bond.

As explained above, numerous thiol compounds have applications in a method for making a carrier. Examples include cysteamine, 1-amino-2-methyl-2-propanethiol, or 1-amino-2-propanethiol, to name only a few.

Moreover, numerous disulfide compounds can be used in a method as set forth above. Preferably, the disulfide compound is symmetric. In a preferred embodiment, the compound is 2,2'-dithiodipyridine.

In addition, a polymer used in a method described above can have a branched or linear structure. Preferably, the polymer is a water soluble polymer. Examples of water soluble polymers having applications in the present invention include polyethylene glycol, carboxymethylcellulose, dextran, polyvinyl alcohol, polyvinyl pyrrolidone, poly-1,3-dioxolane, poly-1,3,6-trioxane, polyaminoacids (homopolymers), polypropylene glycol, copolymers of ethylene glycol/propylene glycol, ethylene/maleic anhydride copolymer, polyaminoacids, copolymer of polyethylene glycol and an amino acid, or polypropylene oxide/ethylene oxide copolymers. In a preferred embodiment, the polymer comprises a copolymer of polyethylene glycol and lysine.

Moreover, a polymer used in methods of making a carrier of the present invention can have any molecular weight. In an embodiment of the present invention, a polymer used in a method of making a carrier for in vivo delivery of a therapeutic agent comprising a thiol group has a molecular weight range of about 1,000 to about 1,000,000 Daltons, and preferably a molecular weight range of about 20,000 to 200,000 Daltons. Preferably, the polymer comprises a molecular weight of about 27,000 Daltons.

The present invention further extends to a method of making a carrier for in vivo delivery of a therapeutic agent comprising a thiol group, wherein the polymer comprises at least one functional group attached thereto available for reaction. Hence, a method of making such a carrier comprise the steps of:

a) reacting the thiol compound with a disulfide compound to form a first intermediate wherein the thiol group of the thiol compound and a sulfur atom of the disulfide bond of the disulfide compound form a disulfide bond; and b) reacting the first intermediate with the polymer comprising at least one functional group attached thereto, to form the carrier comprising the first intermediate conjugated to the at least one functional group attached to the polymer.

After the carrier is formed, it can readily be reacted with a therapeutic agent comprising a thiol group so that its disulfide bond is resolved, and oxidative coupling occurs between the thiol group of the therapeutic agent, and the thiol group of the thiol compound, thereby conjugating the therapeutic agent to the carrier of the present invention via a disulfide bond.

In addition, the at least one functional group of a polymer used in a method of the present invention can be attached to the polymer at an interval. In an embodiment, the interval between functional groups on the polymer is about 100 to about 10,000 Daltons, preferably about 300 to about 3,000 Daltons.

In addition, many methods are known to the skilled artisan to react such compounds to form a first intermediate comprising a disulfide bond in a method of the present invention set forth above. For example, such a reaction can be performed in the presence of an oxidizing agent, such as oxygen, $O_2$, hydrogen peroxide, thallium(III) acetate, $Me_2SOI_2$, bromine under phase transfer conditions, nitric oxide, potassium dichromate, copper, pyridinium chlorochromate (PCC) when dissolved in methylene chloride, to name only a few.

After the first intermediate is formed in the method described above, numerous chemical reactions are available to conjugate the first intermediate to the at least one functional group of the polymer without disrupting the disulfide bond of the first intermediate. For example, such a reaction can be carried out in a polar aprotic solvent, such as N,N-dimethylformamide (DMF), dimethyl sulfoxide (DMSO), dimethylacetamide (DMA). Preferably, the reaction is carried out in a solution comprising DMF, and other reagents such as benzotriazol-1-yl-oxytris(dimethylamino)- phosphonium hexafluorophosphate (BOP) and hydroxybenzotriazol (HOBt). Other reactions apparent to the skilled artisan which conjugate the first intermediate to at least one functional group of a polymer of a carrier of the present invention are encompassed by the present invention.

After the carrier of the present invention is formed, it can be reacted with a therapeutic agent comprising a thiol group, so that the sulfur atom of the thiol compound and the thiol group of the therapeutic agent can form a disulfide bond. This reaction involves reducing the disulfide bond of the carrier so that the sulfur atom of the thiol compound conjugated to the at least one functional group of the polymer undergoes an oxidative coupling with the thiol group of the therapeutic agent. As a result, the therapeutic agent is coupled to a carrier of the present invention via a biodegradable disulfide bond.

Another method of making a carrier for in vivo delivery of a therapeutic agent comprising a thiol group, as set forth herein, comprises the steps of:
 a) reacting a first thiol compound with a second thiol compound to form a first intermediate wherein the thiol group of the first thiol compound and the thiol group of the second thiol compound form a disulfide bond;
 b) reacting the first intermediate with a polymer, to form a second intermediate comprising the first intermediate conjugated to the polymer;
 c) reducing the disulfide bond of the second intermediate to form a third intermediate comprising the polymer and the first thiol compound conjugated to the polymer so that the thiol group of the first thiol compound is available for reaction; and
 d) reacting the third intermediate with a disulfide compound to form the carrier, wherein the thiol group of the first thiol compound and a sulfur atom of the disulfide compound form a disulfide bond.

After the carrier is formed, it can readily be reacted with a therapeutic agent comprising a thiol group. Such a reaction involves reducing the disulfide bond of the carrier, and promoting oxidative coupling between the sulfur atom of the first thiol compound and the thiol group of the therapeutic agent to form a biodegradable disulfide bond.

In an embodiment of the present invention, the first thiol compound and the second thiol compound are the same compound. Hence, the first intermediate can be either a symmetric or asymmetric disulfide compound. Such a reaction can be readily carried out using oxidizing agents set forth above.

Moreover, the conjugation of the first intermediate to the polymer of a carrier of the present invention to form the second intermediate can be carried out in a manner similar to that described above, i.e. in a aprotic polar solvent, with the addition of BOP and HOBt.

The next step of this method of the present invention involves reduction of the disulfide bond of the second intermediate to form the third intermediate. Numerous reducing agents are available to the skilled artisan to reduce the disulfide bond. Examples include lithium aluminum hydride (LiAlH$_4$) in the presence of diethylether, sodium borohydride (NaBH$_4$), glutathione, β-mercaptoethanol, and dithiothrietol (DTT), to name only a few.

Once the thiol group is formed on the third intermediate, it can be reacted with a disulfide compound, in order to form a carrier of the present invention. Preferably, the disulfide compound is symmetric. In an embodiment of the present invention, the compound comprising a disulfide bond is 2,2'-dithiodipyridine. In this embodiment, the disulfide bond of this compound can easily be reduced to form two thiopyridine molecules, one which acts as a leaving group, and one which undergoes oxidative coupling with the thiol group of the third intermediate to form a carrier of the present invention.

An additional step can involve reacting the carrier with a therapeutic compound comprising a thiol group. Such a reaction readily occurs, since the thiopyridine is a stable leaving group. As a result, the therapeutic agent can be conjugated to a carrier of the present invention via a biodegradable disulfide bond, which is difficult to reduce in extracellular fluids in vivo, but is reduced in the cytosol. Hence, a carrier of the present invention provides a therapeutic agent with increased bioavailability relative to bioavailability provided to therapeutic agents with other types of carriers discussed above.

In another embodiment of the present invention, at least one functional group is attached to a polymer of a carrier of the present invention, and is available for reaction. A method of producing a carrier for in vivo delivery of a therapeutic agent comprising a thiol group, comprises the steps of:
 a) reacting a first thiol compound with a second thiol compound to form a first intermediate wherein the thiol group of the first thiol compound and the thiol group of the second thiol compound form a disulfide bond;
 b) reacting the first intermediate with a polymer comprising at least one functional group attached thereto, to form a second intermediate comprising the first intermediate conjugated to the at least one functional group;
 c) reducing the disulfide bond of the second intermediate to form a third intermediate comprising the polymer comprising at least one functional group attached thereto, and the first thiol compound conjugated to the functional group, so that the thiol group of the first thiol compound is available for reaction; and
 d) reacting the third intermediate with a disulfide compound to form the carrier, wherein the thiol group of the first thiol compound and a sulfur atom of the disulfide compound form a disulfide bond.

As explained above, numerous functional groups have applications in a method described above. Examples of functional groups which can be attached to a polymer used of a carrier of the present invention include ketones, esters, carboxylic acids, aldehydes, alcohols, thiols, or amines, to name only a few. In a preferred embodiment of the present invention, the functional group is a carboxylic acid. Moreover, more than one type of functional group can be concurrently attached to a polymer of a carrier of the present invention.

In addition, the least one functional group can be attached to a polymer at an interval. In an embodiment, the interval between functional groups on the polymer is about 100 to about 10,000 Daltons. In a preferred embodiment, the interval between functional groups on the polymer is about 300 to about 3,000 Daltons.

Moreover, numerous thiol compounds have applications in methods of the present invention. For example, thiol compounds such as cysteamine, 1-amino-2-methyl-2-propanethiol, or 1-amino-2-propanethiol can serve as the thiol compound of this method of the present invention, to name only a few.

Further, just as for other methods described above for making a carrier of the present invention, the polymer in this method of the present invention can have a branched or linear structure. Preferably, the polymer is a water soluble polymer. Examples of water soluble polymers having applications herein include polyethylene glycol, carboxymethylcellulose, dextran, polyvinyl alcohol, polyvinyl pyrrolidone, poly-1,3-dioxolane, poly-1,3,6-trioxane, polyaminoacids (homopolymers), polypropylene glycol, copolymers of ethylene glycol/propylene glycol, ethylene/maleic anhydride copolymer, polyaminoacids, copolymer of polyethylene glycol and an amino acid, polypropylene oxide/ethylene oxide copolymers, or polyethylene glycol/thiomalic acid copolymers. In a preferred embodiment, the polymer comprises a copolymer of polyethylene glycol and lysine, which has a carboxylic acid functional group readily available to conjugate a thiol compound to a polymer of a carrier of the present invention.

In addition, a polymer can have any molecular weight. In an embodiment of the present invention, the polymer has a molecular weight range of about 1,000 to about 1,000,000 Daltons, and preferably a molecular weight range of about 20,000 to 200,000 Daltons. In a preferred embodiment, the polymer is a copolymer of polyethylene glycol and lysine, and has a molecular weight of about 27,000 Daltons.

Examples of therapeutic agents comprising a thiol group are also set forth throughout the Specification. However, the present invention and its uses are by no means limited to the examples set forth herein. In particular, disclosed herein are Tat-inhibitory binding peptide derivatives which comprise a thiol group. Hence, they can readily be conjugated to a carrier of the present invention via disulfide bond, and administered in therapeutically effective amounts to treat a mammal suffering from a viral infection, such as AIDS. An example of a Tat-inhibitory peptide derivative having applications in the present invention comprises an amino acid sequence of formula I:

R-Arg-Lys-Lys-Arg-Arg-Gln-Arg-Arg-Arg-X-(biotin)-Cys-NH$_2$ (SEQ ID NO:1)

wherein R is the residue of a carboxylic acid or acetyl group, and X is a Cys or Lys residue, and analogs thereof, and the biologically and pharmaceutically acceptable salts thereof, and stereo, optical and geometrical isomers thereof, where such isomers exist, and pharmaceutically acceptable salts and solvates thereof. Since such agents include a Cys residue, which comprises a thiol group, they can be readily conjugated via a disulfide bond to a carrier of the present invention.

Representative analogs of the polypeptide of formula I thus include:
N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO:3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO:5)
N-acetyl-Gln-Lys-Lys-Arg-Arg-Gln-Arg-Arg-Arg-D-Lys-(biotin)-Cys-NH$_2$ (SEQ ID NO:6)
N-acetyl-Arg-Lys-Lys-Arg-Arg-Pro-Arg-Arg-Arg-Cys-(biotin)-Cys-NH$_2$ (SEQ ID NO:7)

In another example of a therapeutic agent comprising a thiol group which can be conjugated to a carrier of the present invention, disclosed herein is a Tat-inhibitory binding peptide comprising an amino acid sequence as set forth in SEQ ID NO: 8:
N-acetyl-DCys-DLys-(biotin)-DArg-DArg-DArg-DGln-DArg-DArg-DLys-DLys-DArg-NH$_2$ (SEQ ID NO:8)
along with analogs or derivatives thereof, and biologically and pharmaceutically acceptable salts thereof.

Furthermore, as explained above, the present invention extends to a method of treating a viral infection in a mammal in need of such treatment. More particularly, a such a method comprises administering to a mammal a therapeutically effective amount of a therapeutic agent comprising a thiol group, which is conjugated to a carrier for in vivo delivery of a therapeutic agent comprising a thiol group, wherein the carrier comprises a polymer, and at least one thiol compound conjugated to the polymer, such that the thiol group of the thiol compound and the thiol group of the therapeutic agent form a disulfide bond, wherein the therapeutic agent comprises a Tat-inhibitory binding peptide derivative.

Examples of a Tat-inhibitory binding peptide derivative comprises a biotinylated peptide of the formula I:

R-Arg-Lys-Lys-Arg-Arg-Gln-Arg-Arg-Arg-X-(biotin)-Cys-NH$_2$ (SEQ ID NO: 1)

wherein R is the residue of a carboxylic acid or acetyl group, and X is a Cys or Lys residue, and analogs thereof, and the biologically and pharmaceutically acceptable salts thereof, and stereo, optical and geometrical isomers thereof, where such isomers exist.

Moreover, an additional examples of a Tat-inhibitory binding peptide derivative which can be conjugated to a carrier of the present invention, and administered in therapeutically effective amounts to a mammal suffering from a viral infection, such as AIDS, include, but are not limited to:
N-acetyl-Arg-Lys-Lys-Arg-Arg-Gln-Arg-Arg-Arg-Cys-(biotin)-Cys-NH$_2$ (SEQ ID NO:2)
N-acetyl-Arg-Lys-Lys-Arg-Arg-Gln-Arg-Arg-Arg-Lys-(biotin)-Cys-NH$_2$ (SEQ ID NO:3)
N-acetyl-Arg-Lys-Lys-Arg-Arg-Gln-Arg-Arg-Arg-D-Cys-(biotin)-Cys-NH$_2$ (SEQ ID NO:4)
N-acetyl-Arg-Lys-Lys-Arg-Arg-Gln-Arg-Arg-Arg-D-Lys-(biotin)-Cys-NH$_2$ (SEQ ID NO:5)
N-acetyl-Gln-Lys-Lys-Arg-Arg-Gln-Arg-Arg-Arg-D-Lys-(biotin)-Cys-NH$_2$ (SEQ ID NO:6), or
N-acetyl-Arg-Lys-Lys-Arg-Arg-Pro-Arg-Arg-Arg-Cys (biotin)-Cys-NH$_2$ (SEQ ID NO:7) to name only a few.

Another example of a therapeutic agent comprising a thiol group which is conjugated to a carrier of the present invention and can be used in treating a viral infection in a mammal in need of such treatment, comprises an amino acid sequence set forth in SEQ ID NO:8:
N-acetyl-DCys-DLys-(biotin)-DArg-DArg-DArg-DGln-DArg-DArg-DLys-DLys-DArg-NH$_2$ (SEQ ID NO:8)
along with analogs or derivatives thereof and pharmaceutically acceptable salts thereof.

In particular, the method can be used to treat retroviral infections such as AIDS in humans.

Numerous methods are presently available for administering the carrier of the present invention to a mammal, which will produce a therapeutic effect therein. For example, a pharmaceutical composition can be formed comprising a carrier of the present invention conjugated to a Tat-inhibitory peptide derivative, and a pharmaceutically acceptable carrier thereof. Moreover, according to the invention, the carrier conjugated to a Tat-inhibitory peptide derivative, or a pharmaceutical composition as described above, may be introduced parenterally, transmucosally, e.g., orally, nasally, or rectally, or transdermally. Preferably, administration is parenteral, e.g., via intravenous injection, and also includes, but is not limited to, intra-arteriole, intramuscular, intradermal, subcutaneous, intraperitoneal, intraventricular, and intracranial administration.

In another embodiment, the carrier of the present invention is conjugated to a Tat-protein inhibitory polypeptide derivative, or pharmaceutical composition comprising such a conjugated species, can be delivered in a vesicle, in particular a liposome [see Langer, *Science* 249:1527–1533

(1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.].

In yet another embodiment, the therapeutic agent, such as a Tat-protein inhibitory polypeptide derivative can be conjugated to a carrier of the present invention, which can then be delivered in a controlled release system. For example, as explained above, functional groups attached to a thiol group of a carrier of the present invention produce steric hindrance which reduces the rate at which a disulfide bond conjugating the therapeutic agent to a carrier of the present invention is reduced. Hence the rate at which a Tat-protein inhibitory polypeptide derivative is released from the carrier, and delivered to a target cell or tissue can be modulated, depending on the structure of the thiol compound of the carrier. Other ways of delivering the therapeutic agent in a controlled release system include administration via intravenous infusion, an implantable osmotic pump, a transdermal patch, liposomes, or other modes of administration. In one embodiment, a pump may be used [see Langer, supra; Sefton, *CRC Ctit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)].

The following example is presented in order to more fully illustrate the invention. It should in no way be construed, however, as limiting the broad scope of the invention.

EXAMPLE

As explained above, covalent attachment of water-soluble polymers can be used to manipulate pharmacologic properties of a therapeutic agent. For example, appending polyethylene glycol (PEG) chains to a protein can increase its circulating half-life and minimize its immunologic properties[2]. Other researchers have designed a PEG-lysine copolymer having multiple attachment sites[3]. The researchers then prepared conjugates through either biostable or biodegradable linkages[3], but did not investigate the biodegradable disulfide linkage. This linkage can be especially useful for drug delivery into cells, due to the stronger reducing environment within cells than in extracellular fluids. Disclosed herein is a carrier for in vivo delivery of a therapeutic agent comprising a thiol group, in which the carrier has multiple attachment sites for forming a disulfide bond with a therapeutic agent. Disulfide bonds have heretofore not been used as a biodegradable linkage between a therapeutic agent and a synthetic polymer carrier, nor in combination with a cell uptake promoter.

Materials and Methods

Cysteamine hydrochloride, Ellman's reagent [5,5'-dithiobis(2-nitrobenzoic acid) and glutathione (reduced form) were obtained from Sigma Chemicals (St. Louis, Mo.). Dithiothreitol (DTT) was obtained from Pierce (Rockford Ill.). 2,2'-dipyridyl disulfate, 1-amino2-methyl-2-propanethiol, diisopropylethyl amine (DIEA) and silica gel, 70–230 mesh, 60A were obtained from Aldrich Chemical (Milwaukee, Wis.). Hydroxybenzotriazol (HOBt), benzotriazol-1-yloxytris(dimethylamino)phosphonium hexafluorophosphate (BOP) and dimethylformamide (DMF) were obtained from PerSeptive Biosystems (Boston, Mass.). Dichloromethane (DCM) and methanol (MeOH) were HPLC grade and obtained from Fisher Scientific (Pittsburgh, Pa.). "SEPHADEX" gel filtration beads were obtained from Pharmacia LKB Biotechnology (Piscataway, N.J.). Polyethylene glycol-lysine copolymer with a molecular weight of about 27 kDa, (Molecular Weight=2.69×10$^4$ D, 2198 D/repeating unit), was synthesized according to a published procedure[3].

Peptide Synthesis

Small peptides were synthesized and used herein as therapeutic agents comprising thiol groups. The peptide N-acetyl-Phe-Arg-Arg-Arg-Cys-NH$_2$ (SEQ ID NO:9) was synthesized at Louisiana State University (LSU) core facility using Fmoc chemistry, purified by reverse-phase HPLC and confirmed for structure by mass spectral analysis.

The peptides N-acetyl-Arg-Lys-Lys-Arg-Arg-Gln-Arg-Arg-Arg-Cys-NH$_2$ (SEQ ID NO:10), and N-acetyl-Arg-Lys-Lys-Arg-Arg-Gln-Arg-Arg-Arg-Lys-(biotin)-Cys-NH$_2$ (SEQ ID NO:3) were manually synthesized using Fmoc chemistry. For radiolabeling, the assembled peptide on the solid support was allowed to react with tritiated acetic anhydride in the presence of the coupling activation reagents, BOP, HOBt, and DIEA. Acetylation of the peptide was completed by chasing with an excess of non-radioactive acetic anhydride.

After cleavage from the solid support followed by ether precipitation, the radiolabeled peptide was purified by chromatography on "SEPHADEX" gel filtration beads size G-10 using PBS (0.15 M NaCl, 20 mM potassium phosphate buffer, pH 7.4) for elution or by centrifugal concentration using a "CENTRICON-10" ultrafilter (Amicon/Millipore, Bedford, Mass.).

Preparation of a Carrier of the Present Invention with Scheme I

To a solution of cysteamine hydrogen chloride (0.50 g, 4.4 mmole) dissolved in 15 ml degassed buffer (0.1 N sodium acetate adjusted to pH 4.0 with acetic acid, 0.3 M sodium chloride, 1 mM EDTA) was added 2,2'-dithiodipyridine (3.5 g, 15 mmol; dissolved in 18 ml MeOH). The mixture was stirred at room temperature under N$_2$. The reaction, which was monitored with thin layer chromatography (ammonium hydroxide/MeOH (methanol)/DCM (dichloromethane): Feb. 10, 1990), was complete after 4 h. The MeOH was removed in vacuo and the residue was made basic by saturating with sodium carbonate. The residue was extracted into DCM (3×50 ml) and the combined DCM was washed with water (2×40 ml) and brine (40 ml) and then dried over magnesium sulfate. The magnesium sulfate was filtered and the filtrate was concentrated in vacuo to an oily residue. The product, cysteamine-thiopyridine (the first intermediate of scheme I), was purified by flash chromatography on a silica gel column (ammonium hydroxide/MeOH/DCM: Feb. 10, 1990). Yield: 0.30 g (yellow oil) (36%). $^1$HNMR (CDC$_{13}$) δ 8.4–8.5 ppm (m,1H), 7.7–7.6 ppm (m,2H), 7.15–7.0 ppm (m,1H), 3.0–2.7 ppm (m, 4H), 0.9 ppm (b, 2H).

The polymer comprising PEG-lysine copolymer (0.20 g, 91 μmol lysine) was dissolved in 2.5 ml of degassed DMF. Cysteamine-TP (the first intermediate) (0.5 mmol), BOP (0.5 mmol), HOBt (0.5 mmol) and DIEA (25 μl) were added to the solution comprising the polymer, and stirred under N$_2$ overnight. In this reaction, the first intermediate conjugates with the at least one carboxylic acid available for reaction attached to the polymer to form the second intermediate. Since numerous free carboxylic acids are present on the polymer, more than one first intermediate can be conjugated to the polymer.

The product (a carrier of the present invention) was precipitated with cold ether, washed with cold ether and then dried by Speedvac (Savant Instrument Co., Farmingdale, N.Y.) to a gel-like residue. The product was dissolved, and purified on a "SEPHADEX" gel filtration G-75 column (48 ml bed volume) using 0.1 N acetic acid. Appropriate fractions were combined and lyophilized. Yield: 0.11 g (colorless solid). Once the carrier has been purified, it can be reacted with a therapeutic agent comprising a thiol group so that the disulfide bond of the carrier is reduced, and a new disulfide bond can be formed conjugating the therapeutic agent to the carrier.

Preparation of a Carrier of the Present Invention with Scheme II

As stated above, in this method, the first thiol compound and the second thiol compound can be the same chemical compound. Hence, in this example, two cysteamine hydrogen chlorides were first converted to a disulfide-linked dimer by overnight stirring of an in air aqueous solution (0.3 g in 15 ml) adjusted to pH 8.6 with triethylamine. Ellman's assay indicated less than 1% remaining-free thiol. To the mixture was added a saturated solution of sodium carbonate to pH 10, followed by extracting into DCM (5×20 ml), drying over magnesium sulfate, filtering and concentrating on a rotary evaporator. As a result, a first intermediate was formed which is a symmetric disulfide.

PEG-lysine copolymer (0.20 g, 91 micromol of lysine, molecular weight $2.69 \times 10^4$ D) was dissolved in 2.5 ml of degassed DMF. The cysteamine dimer (the first intermediate) (650 µmole), BOP (650 µmole), HOBt (650 µmole) and DIEA (25 µl) were added to the PEG copolymer solution and stirred under $N_2$ overnight. The product was precipitated with cold ether, washed with cold ether and then dried by Speedvac to a gel. The product, the second intermediate, was purified on a "SEPHADEX" G-75 gel filtration column, as above. Appropriate fractions were combined and lyophilized to give 70 mg of colorless solid, which was dissolved in degassed PBS (pH 7.4).

DTT (10 molar equivalents based on lysine) was then added to reduce the disulfide bond of the second intermediate, and the reduction reaction proceeded under $N_2$ overnight. The product, the third intermediate, was purified on a G-75 column (48 ml bed volume) using 0.1 N acetic acid containing 1 mM EDTA for elution. Appropriate fractions were combined and lyophilized to give 60 mg of colorless solid, which was dissolved in 4 ml of degassed buffer (0.1 N sodium acetate adjusted to pH 4 with acetic acid, 0.3 M sodium chloride, 1 mM EDTA).

2,2'Dithiopyridine (270 µmole) dissolved in 3 ml of degassed MeOH was added and the reaction mixture was stirred under $N_2$ for 2 h. The MeOH was removed on a rotary evaporator and the product (the carrier) was purified on a "SEPHADEX" G-75 gel filtration column (bed volume 48 ml) using 0.1 N acetic acid for elution. Appropriate fractions were combined, and lyophilized to give 30 mg of colorless solid. The carrier, which at this point is an asymmetric disulfide, can readily be reacted with a therapeutic agent comprising a thiol group so that its disulfide bond can be reduced, and the therapeutic agent can be conjugated to the carrier of the present invention via a disulfide bond. A similar procedure was used to prepare the PEG derivative of the sterically hindered cysteamine analog, 1-amino-2-methyl-2-propanethiol. The use of the sterically hindered cysteamine analog in a carrier of the present invention can modulate the rate of release of a therapeutic agent from the carrier. In particular, the addition of the 2 methyl groups to cysteamine causes steric hindrance. Applicants have discovered this hindrance reduces the rate at which the disulfide bond conjugating a therapeutic agent to a carrier of the invention is reduced. As a result, the rate at which the therapeutic agent is released from the carrier is reduced. This reduction of rate of release is dependent upon the steric hindrance of the thiol compound conjugated to the polymer of a carrier of the present invention.

Determination of the 2-Thiopyridine Content in PEG-S-S-TP.

The concentration of a PEG-S-S-TP solution was determined by acid hydrolysis and measurement of the released lysine using an Applied Biosystems amino acid analyzer (LSU core facility). Varying amounts of PEG-S-S-2TP (100, 200 and 400 µl) of a 4 mg/ml (ca. 2 mol/ml of lysine) solution in water were reacted separately with an excess of DTT (200 µl of 26 mole/ml in water) and diluted to a final volume of 1.0 ml with PBS. The amount of 2-thiopyridone liberated was quantitated using a molar extinction coefficient of $7.06 \times 10^3$ at 343 nm (5). The ratio of Thiopyridine to lysine was then calculated.

Preparation of PEG-Cysteamine-Peptide.

PEG-cysteamine-TP (an example of a carrier of the present invention prior to its conjugation via a disulfide bond to a therapeutic agent comprising a thiol group), dissolved in water (8 µmole/ml of lysine), was mixed with an equal volume of PBS containing 1 mM EDTA. To 3 ml of this solution was added 1 equivalent (as determined by Ellman's assay for thiolse) of the peptide, N-acetyl-Phe-Arg-Arg-Arg-Cys-NH$_2$ (SEQ ID NO:9). The reaction, which was monitored at 343 nm on aliquots of the mixture, was complete after 15 minutes of stirring under $N_2$. The product was purified on a Sephadex G-75 column, using PBS as eluent. Appropriate fractions were pooled. The extent of peptide derivatization of the copolymer was determined by amino acid analysis (LSU core facility). Radiolabeled peptides were appended to PEG-cysteamine-TP and purified on a G-75 column in a similar manner, but on a smaller scale.

Release of Peptides from a Carrier of the Present Invention

The disulfide linked conjugate, PEG-cysteamine-N-acetyl-Phe-Arg-Arg-Arg-Cys-NH$_2$ (SEQ ID NO:9) was added to a solution of reduced glutathione (3 mM in PBS) to a final peptide concentration of 0.3 mM, and then incubated under $N_2$ at room temperature. A sample was taken at each time point, acidified by adding an aliquot of 5% TFA and applied to a G-75 column in 0.1% TFA (7 ml bed volume) to separate PEG-conjugated peptide from free peptide. Appropriate fractions in the high-molecular-weight region were pooled, and the extent of peptide derivatization at each time point was determined by amino acid analysis. For measuring the release of radiolabeled peptide, each time point aliquot was acidified to pH 3.5 with sulfuric acid. The PEG-conjugated peptide and the free peptide were then separated using ultrafiltration on "CENTRICON-10". To ensure complete separation, the retentate was diluted and ultrafiltered two more times. Radioactivity in the retentate and combined filtrate was quantitated by scintillation counting.

RESULTS

Preparation of a Carrier of the Present Invention Conjugated to a Therapeutic Agent Comprising a Thiol Group The synthetic routes are given in Schemes 1 and II. In Scheme 1, cysteamine, the thiol compound, was first converted into the mixed disulfide with 2-thiopyridine, forming the first intermediate. The cysteamine-TP reagent was purified by silica gel chromatography and its structure was confirmed by $^1$H-NMR. It was found to be necessary to use this reagent immediately for coupling to the PEG-lysine copolymer, since the 2-thiopyridone would react back to 2,2-dipyridyldisulfide, as evaluated by NMR, at a rate of about 15%/day. Amide bond formation between the carboxylate groups on the PEG-lysine copolymer and the amino group on cysteamine was accomplished using reagents typically used for coupling in peptide synthesis (Scheme I).

In Scheme II, cysteamine (the first and second thiol compounds in the example) is first converted to the symmetric disulfide (the first intermediate of this method), then appended to the PEG-lysine polymer forming the second intermediate. The disulfide bond of the second intermediate is then reduced to form the third intermediate comprising a thiol group. In the last step, the third derivative is reacted with 2,2'-dithiodipyridine to produce a carrier of the present invention prior to its conjugation to a therapeutic agent comprising a thiol group. Hence at this point, the carrier comprises a disulfide bond.

Figure 3:
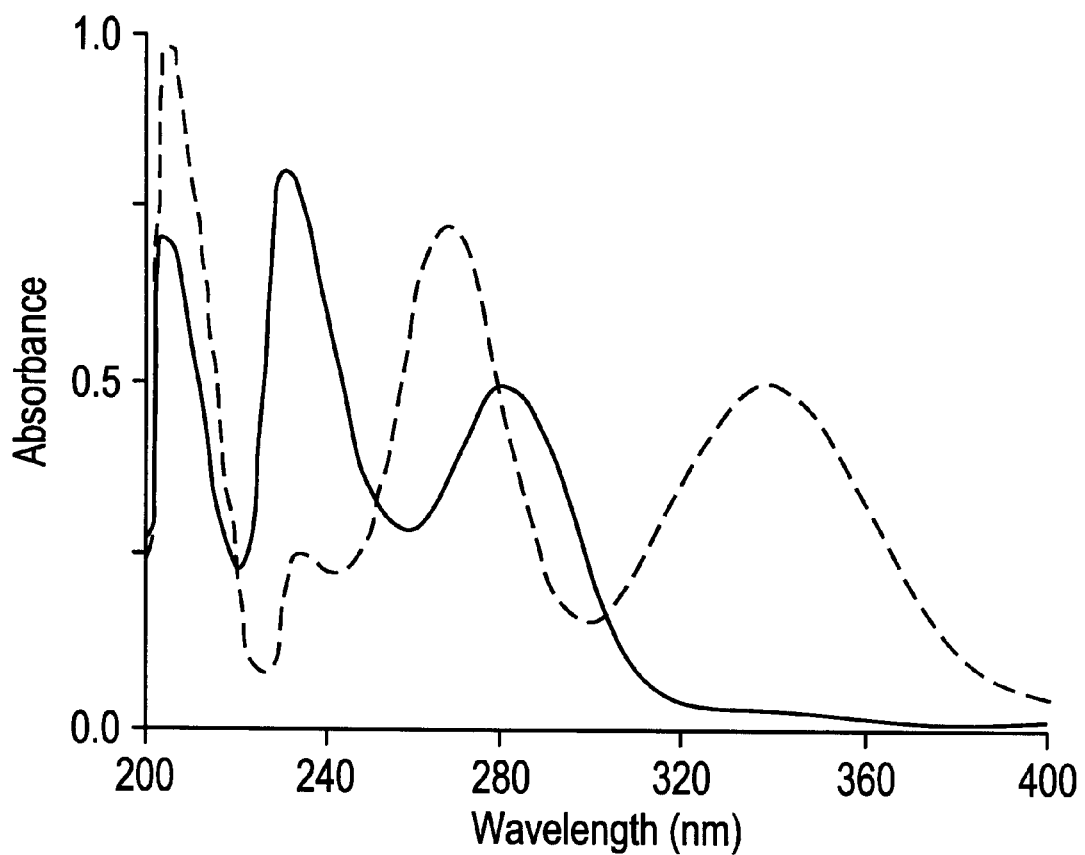
FIG. 3 is a spectroscopic analysis of the reaction of PEG-cysteamine-thiopyridine (PEG-cysteamine-TP) with the peptide N-acetyl-Phe-Arg-Arg-Arg-Cys-NH$_2$ (SEQ ID NO:9). The UV spectrum of the solution of PEG-cysteamine-TP is shown (solid line). Addition of the peptide results in the release of 2-thiopyridone, which is observed as a peak with a maximum at 343 nm (dashed line).
Figure 4:
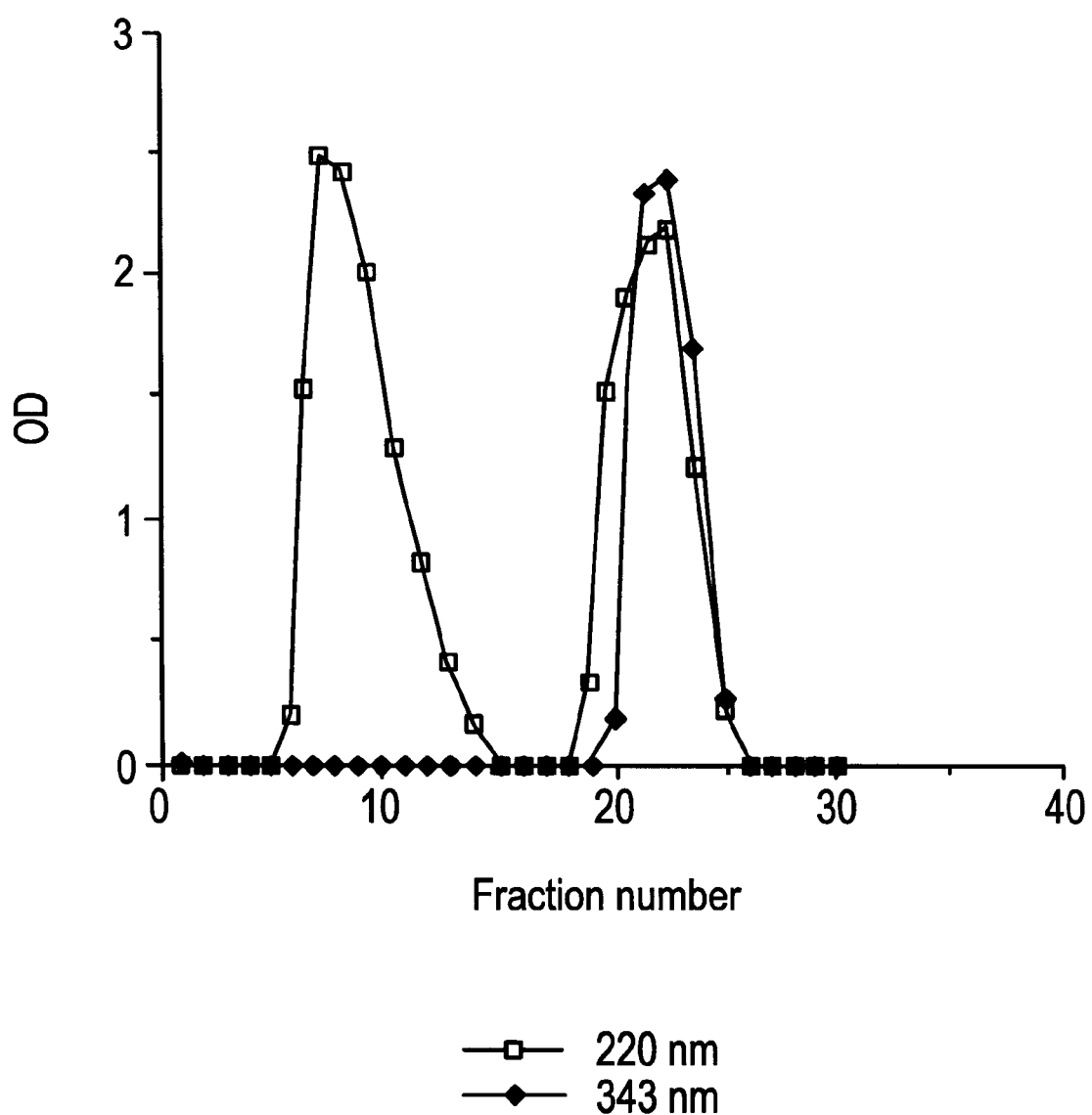
FIG. 4 is a graph showing the purification of the product from the reaction mixture of PEG-cysteamine-TP and the peptide N-acetyl-Phe-Arg-Arg-Arg-Cys-NH$_2$ (SEQ ID NO:9) by gel filtration chromatography. Note the presence of the released 2-thiopyridine in the low-molecular weight fractions according to the absorbance at 343 nm.

The disulfide bond between 2-thiopyridine and cysteamine appended to PEG-lysine polymer of the carrier is stable to hydrolysis in PBS (pH 7.4), as determined by absence of absorbance at 343 nm after 24 hours at room temperature. However, upon addition of a cysteinyl-peptide, such as N-acetyl-Phe-Arg-Arg-Arg-Cys-NH$_2$ (SEQ ID NO:9), the reaction was complete within several minutes, as determined by the released 2-thiopyridone group, measured at 343 nm (FIG. 3). With regard to stoichiometry, the amount of 2-thiopyridone released from a given amount of PEG/Lys-S-S-TP solution by an excess of reducing agent (DTT) in PBS was determined. One equivalent (as defined by thiol groups measured by Ellman's assay) of the peptide, N-acetyl-Phe-Arg-Arg-Arg-Cys-NH$_2$ (SEQ ID NO:9), was then added to an aliquot of PEG/Lys-S-S-TP solution, and the reaction was found to be essentially complete according to released 2-thiopyridone. Purification of the product, PEG/Lys-S-S-PEPTIDE, by gel filtration chromatography gave complete separation from released 2-thiopyridone and, presumably, from any residual unreacted peptide (FIG. 4).

Acid hydrolysis, followed by amino acid analysis was used to determine the concentration of a sample of the PEG-lysine copolymer, and treatment with an excess of i)TT was used to determine the amount of coupled cysteamine-S-S-TP on that same sample. By this procedure, it was determined that 66+/−8% of the lysine carboxylate groups had been derivatized with cysteamine-TP on a sample of PEG/Lys cysteamine-TP prepared by Scheme I. Acid hydrolysis, followed by amino acid analysis was also used to determine the extent of derivatization by the peptide, N-acetyl-Phe-Arg-Arg-Arg-Cys-NH$_2$ (SEQ ID NO:9). Duplicate analyses gave a ratio of Phe:Lys of 0.64 and 0.55, and of Arg:Lys of 2.0 and 1.8. Therefore, the extent of peptide derivatization, based on lysine groups, was 62+/−4%. In another sample prepared by Scheme I, the peptide coupling ratio was found to be 66+/−31%. In a sample prepared by Scheme II, the peptide coupling ratio was found to be 78+/−9%.

Release Studies

Release of the peptide, N-acetyl-Phe-Arg-Arg-Arg-Cys-NH$_2$ (SEQ ID NO:9), by reductive cleavage of its disulfide linkage to a carrier of the present invention comprising a PEG/Lys copolymer was evaluated using 3 mM glutathione in PBS (pH 7.4) at room temperature. At each time point, an aliquot was withdrawn and acidified to halt the disulfide interchange reaction. Released peptide was removed from PEG/Lys-peptide conjugate by gel filtration chromatography, and the ratio of PEG (i.e. Lys residues) to peptide (i.e. Phe or Arg residues) was determined by amino acid analysis. Release was found to be relatively rapid, with a half-time of about 3 minutes. The presence of glycine and glutamic acid in the high-molecular-weight glutathione-treated samples (data not shown) indicates that glutathione replaces the released peptide on the PEG copolymer.

Figure 5:
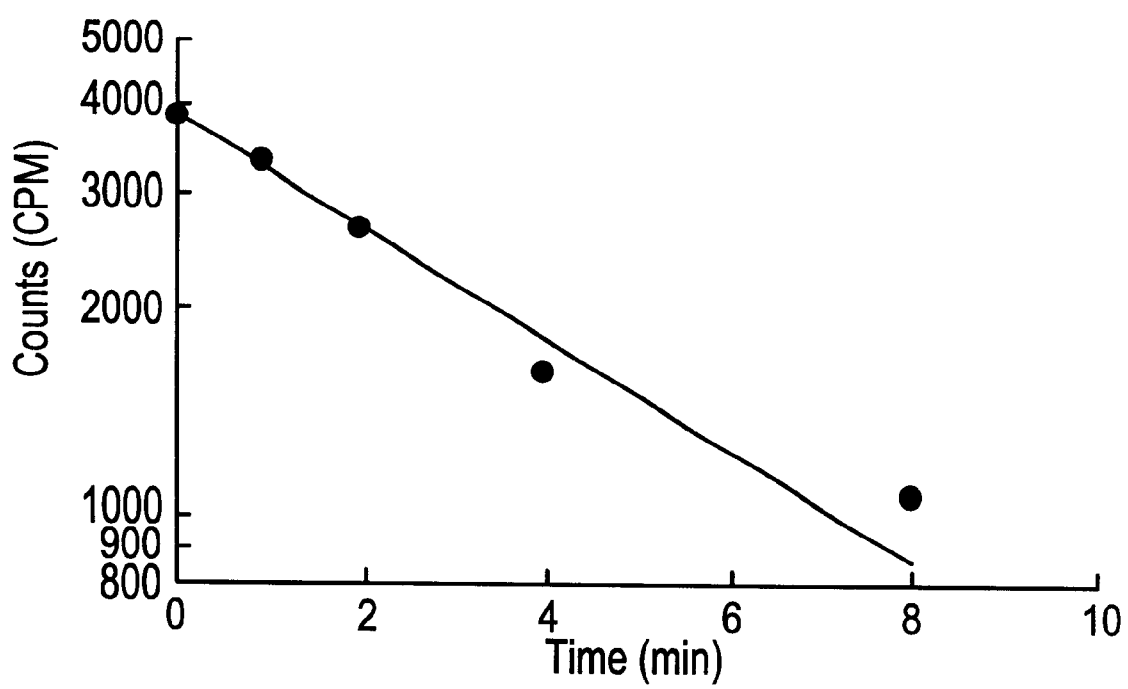
FIG. 5 is a graph of a time course release of a radiolabeled peptide from PEG-cystemaine-peptide by 3 mM glutathione in PBS. The data is presented as a semi-log plot. Essentially the same release kinetics were obtained in two additional experiments.

Release kinetics were also studied using the disulfide-linked radiolabeled peptides, N-acetyl-Arg-Lys-Lys-Arg-Arg-Gln-Arg-Arg-Arg-Cys-NH$_2$ (SEQ ID NO: 10) and N-acetyl-Arg-Lys-Lys-Arg-Arg-Gln-Arg-Arg-Arg-Lys-(biotin)-Cys-NH$_2$ (SEQ ID NO:3). Released peptide was removed from PEG/Lys-peptide conjugate by ultrafiltration. The half time of release in PBS containing 3 mM glutathione was found to also be about 3 minutes for either peptide (FIG. 5).

Figure 6:
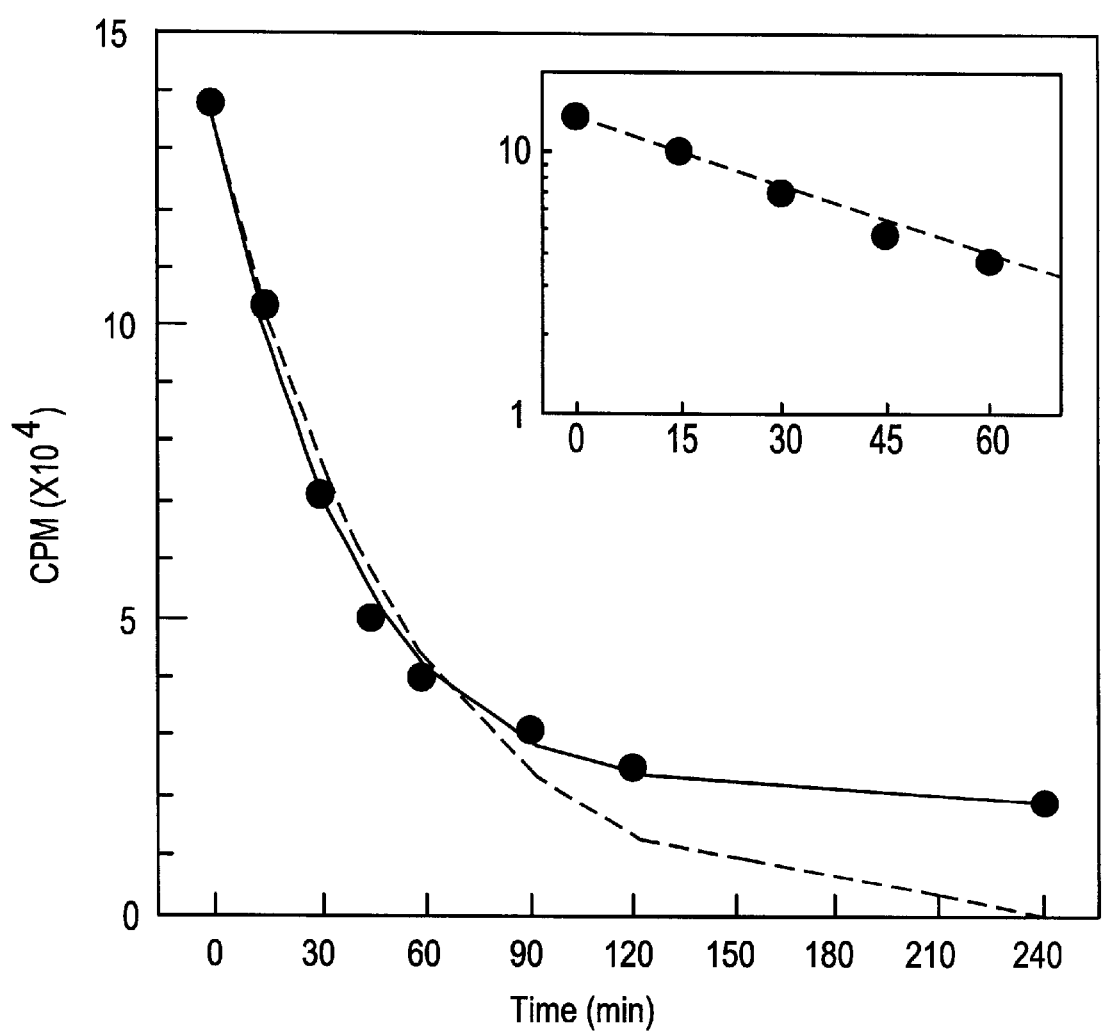
FIG. 6 is a graph of a time course release of a radiolabeled peptide from PEG-1-amino-2-methyl-2-propanethiol-peptide by 30 mM glutathione in PBS. The dashed line is a theoretical plot of $C=C_{initial}e^{-kt}$ A semi-log plot of the early time point data is shown in the inset. Essentially the same release kinetics were obtained in two additional experiments.

To achieve a slower release rate, as previously suggested for linking antibodies to toxins[7], the PEG/Lys derivative of the sterically hindered cysteamine analog, 1-amino-2-methyl-2-propanethiol, was synthesized. Analysis of the release rate of the radiolabeled peptide, N-acetyl-Arg-Lys-Lys-Arg-Arg-Gln-Arg-Arg-Arg-Lys-(biotin)-Cys-NH$_2$ (SEQ ID NO:3) gave a half-time of about 40 min in the presence of 30 mM glutathione (FIG. 6). Since the disulfide cleavage rate is proportional to glutathione concentrations, the sterically hindered linker has a release rate about 100 times slower than does a carrier of the present invention in which the thiol compound is cysteamine. Thus, the release rate can be readily controlled by selection of a thiol compound having functional groups, wherein the thiol compound is conjugated to the polymer, and conjugated via a disulfide bond to a therapeutic agent.

Bioavailability of Therapeutic Agents Conjugated to a Carrier of the Present Invention In order to determine the effect of a carrier of the present invention on bioavailability of a therapeutic agent conjugated thereto, a Tat-inhibitory polypeptide derivative, having an amino acid sequence of N-acetyl-Arg-Lys-Lys-Arg-Arg-Gln-Arg-Arg-Arg-Lys-(biotin)-Cys-NH$_2$ (SEQ ID NO:3) was conjugated to a carrier of the present invention via a disulfide bond through an eleventh residue of cysteine. The carrier of the present invention used in this example comprised a polymer comprising a polyethylene glycol/lysine copolymer with a molecular weight of about 27,000 D ($2.69 \times 10^4$ D). The at least one thiol compound conjugated to the polymer was cysteamine. In particular, cysteamine was conjugated to the carboxylic acid group of lysine of the polymer (hereinafter referred to as the "cysteamine-PEG carrier").

An experiment was then performed to compare the potency of the amino acid sequence of SEQ ID NO:3 alone to inhibit Tat binding to TAR RNA with the potency of the amino acid sequence of SEQ ID NO:3 conjugated to a carrier of the present invention to inhibit Tat binding to TAR RNA. The results of this experiment are set forth in FIG. 7.

Figure 7:
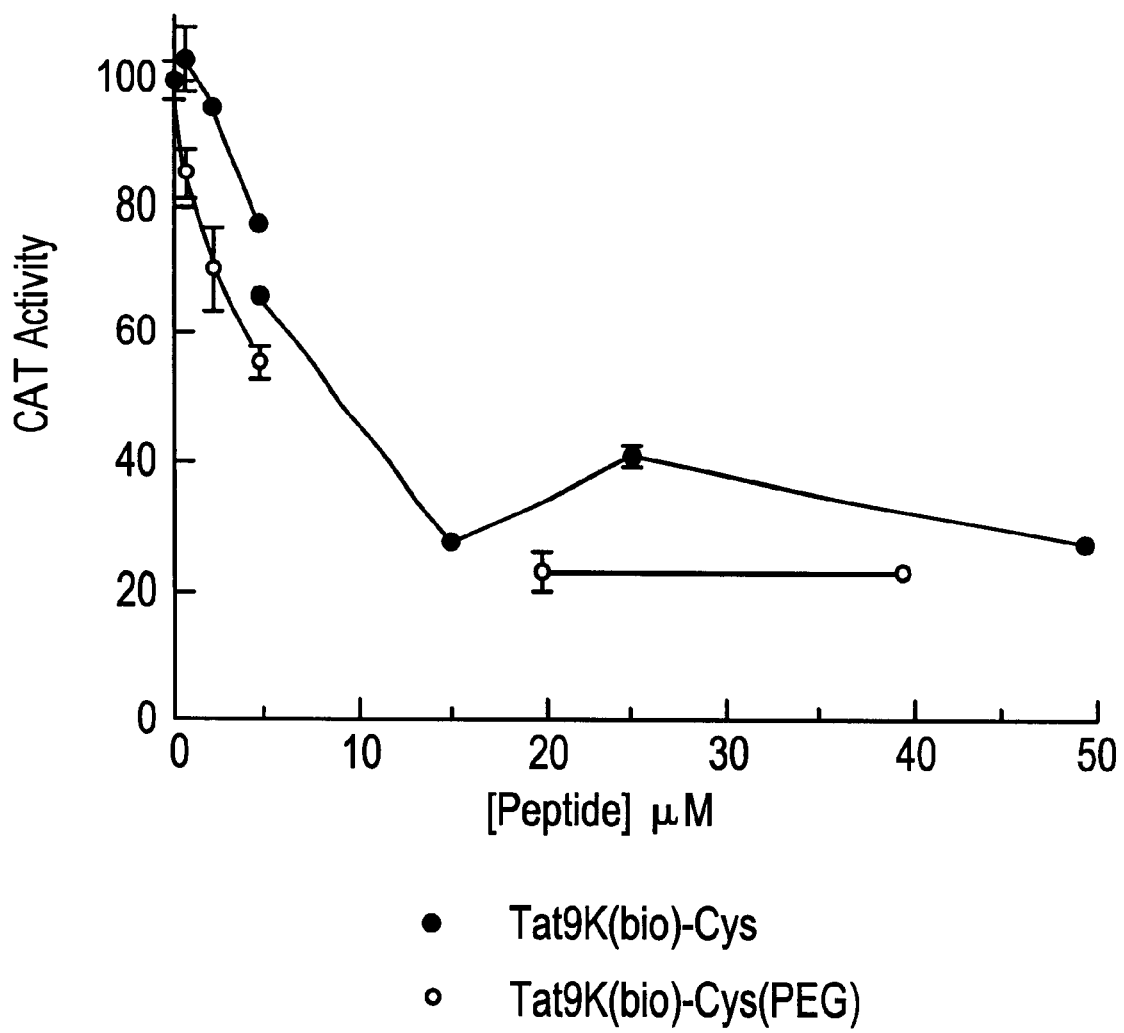
FIG. 7 is a graph of the comparison of the inhibition of protein expression in a Jurkat cell line transfected with a TAR-CAT (TAR-Chloramphenicol Acetyl Transferase) plasmid and a Tat-protein plasmid. In this experiment, one group of cells was administered a Tat inhibitory biotinylated polypeptide derivative having a sequence of N-acetyl-Arg-Lys-Lys-Arg-Arg-Gln-Arg-Arg-Arg-Lys-(biotin)-Cys-NH$_2$ (SEQ ID NO:3), and another group of cells was administered the same Tat inhibitory biotinylated peptide derivative conjugated to a carrier of the present invention via a disulfide bond between the sulfur atom of the thiol group of the thiol compound, and the the thiol group of the Cys residue located between biotin and the amino group of the Tat inhibitory biotinylated polypeptide derivative of SEQ ID NO: 3. The polymer of the carrier used in this experiment had a molecular weight of about 27,000 D (6.29×10$^4$) and comprised a copolymer of polyethylene glycol (PEG) and lysine. Cysteamine was the thiol compound conjugated to the polymer. Conjugation of cysteamine to the polymer involved the carboxylic acid group of the lysine incorporated into the copolymer, which was available for reaction. If the polypeptide was successful in inhibiting Tat binding to TAR, CAT would be produced. Hence, an assay of CAT was used to measure inhibition.

Initially, a Jurkat cell line was stably transfected with a TAR-CAT plasmid. At time (t)=0, the cells were transfected with a Tat-protein plasmid. The cells were then grown in 10% fetal calf serum for about 18 hours. At t=18 hours, the biotinylated Tat peptide inhibitor, having a sequence of SEQ ID NO:3, either free or appended to a carrier of the present invention via disulfide bond, wherein the carrier comprised a PEG/Lys copolymer having a molecular weight of about 27,000 D ($2.69\times10^4$ D) with cysteamine conjugated to the polymer, and a disulfide bond formed between the inhibitor having an amino acid of SEQ ID NO:3 and cysteamine, was added at each indicated concentration set forth in x axis of the graph of FIG. 7. At t=42 hours, the cells were harvested and CAT protein was measured by immunoassay. Each data point set forth in FIG. 7 is the average of 3 separate cell cultures. The data for the low concentrations of free and appended peptide were obtained in a side-by-side experiment, whereas the data for the high concentrations were obtained in separate experiments. The remaining 20–25% of CAT activity at high inhibitor concentrations most likely represents CAT protein already synthesized prior to addition of the inhibitor to the culture media and its uptake by the cells.

Surprisingly, the biotinylated Tat-peptide inhibitor (comprising an amino acid sequence of SEQ ID NO:3) appended to a carrier of the present invention had an additional about 5-fold increase in potency relative to the potency of the biotinylated Tat-peptide inhibitor administered alone. Hence, a carrier of the present invention contributes to enhanced potency and bioavailability of a therapeutic agent comprising a thiol group.

DISCUSSION

Disclosed herein are carriers for in vivo delivery of a therapeutic agent, wherein the therapeutic agent is reversibly linked to a carrier of the present invention, and methods for making such carriers. The reversible linkage is a disulfide bond, which can be cleaved by glutathione, a physiologically relevant reducing agent found predominantly in cellular cytosol.

In particular, release of a therapeutic agent, such as a peptide, from a carrier of the present invention was studied in PBS containing 3 mM reduced glutathione, which is the approximate concentration found in the cells of most tissues[9]. Since the concentration of reduced glutathione in blood is on the order of 10 $\mu M^{10}$, a therapeutic agent conjugated to a carrier of the present invention via a disulfide bond should remain mostly bound to a carrier of the present invention in an extracellular environment. More importantly, therapeutic agents should be released from a carrier of the present invention upon entry into cells.

Moreover, the peptide, N-acetyl-Arg-Lys-Lys-Arg-Arg-Gln-Arg-Arg-Arg-Lys-(biotin)-Cys-NH$_2$ (SEQ ID NO:3), used in the examples disclosed herein, represents a Tat-inhibitory peptide derivative, as set forth above. The appended biotin moiety has been found to increase cell uptake of the peptide[11]. Such a cell uptake promoter can be appended either to the therapeutic agent, or to the polymer of a carrier of the present invention. Hence, a carrier of the present invention provides a vehicle for reaching intracellular disease-related targets with therapeutic agents that would otherwise not have the requisite pharmacological properties to cross a cell membrane. The appended Cys serves as the thiol group of the therapeutic agent for forming the disulfide bond with the carrier.

In addition, data set forth in FIG. 7 clearly indicates a therapeutic agent has increased potency when conjugated to a carrier of the present invention. Such increased potency is a reflection of protection and increased bioavailability the carrier of the present invention provides to a therapeutic agent conjugated to it.

While the invention has been described and illustrated herein by reference to various specific materials, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

1. Duncan, R. and Kopacek, J. (1984) Soluble synthetic polymers as potential drug carriers. *Adv. Polym. Sci.* 57, 53–101.
2. Davis, S., Abuchowski, A., Park, Y. K. and Davis, F. F. (1981) Alteration of the circulating half life and antigenic properties of bovine adenosine deaminase in mice by attachment of polyethylene glycol. *Clin. Exp. Immunol.* 46, 649–652.
3. Nathan, A., Zalipsky, S., Ertel, S. I., Agathos, S. N., Yarmush, M. L. and Kohn, J. (1993) Copolymers of lysine and polyethylene glycol: A new family of functionalized drug carriers. *Bioconj. Chem.* 4, 54–62.
4. Woghiren, C., Sharma, B. and Stein, S. (1993) Protected thiolpolyethylene glycol: A new activated polymer for reversible protein modification. *Bioconj. Chem.* 4, 314–318.
5. D. R. Grassetti and J. F. Murray. J. R. (1967) Determination of sulfhydryl groups with 2,2'- or 4,4'-dithiodipyridine. *Arch. Biochem. Biophys.* 119, 41–49.
6. Riddles, P.W., Blakeley, R.L., and Zerner, B. (1979) Ellman's reagent:5,5'Dithiobis(2-nitrobenzoic acid)-a reexamination. *Anal. Biochem.* 94, 75–81.
7. Goff, D. A. and Carroll, S. F. (1990) Substituted 2-iminothiolanes: Reagents for the preparation of disulfide cross-linked conjugates with increased stability. *Bioconj. Chem.* 1, 381–386.
8. Trimble, S. P., Marquardt, D. and Anderson, D. C. (1997) Use of designed peptide linkers and recombinant hemoglobin mutants for drug delivery: In vitro release of an angiotensin II analog and kinetic modeling of delivery. *Bioconj. Chem.* 8, 416–423.
9. Meister, A., Griffith, O. W. and-Tate, S. S. (1979) New aspects of glutathione metabolism and translocation in mammals. *Ciba Foundation Symposium* 72, 135–161.
10. Meister, A. (1991) Glutathione deficiency produced by inhibition of its synthesis and its reversal; applications in research and therapy. *Pharmacol. Ther.* 51, 155–194.
11. Choudhury, I., Wang, J., Rabson, A. B., Stein, S., Pooyan, S., Stein, S. and Leibowitz, M. J. (1998) Inhibition of HIV-1 replication by a Tat RNA binding domain peptide analog. *J. Acqu. Immune Def. Syndr. & Human Retrovirol.*, 17, 104–111.

Moreover, any previously cited references are also incorporated by reference in their entirety.

Many other variations and modifications of the invention will be apparent to those skilled in the art without departing from the scope of the invention. The above-described descriptions are, therefore, intended to be merely exemplary, and all such variations and modifications are intended to be included within the scope of the invention as defined in the

What is claimed is:

1. A carrier for in-vivo delivery of a therapeutic agent comprising a thiol group, wherein said carrier comprises:
   a) a polymer;
   b) multiple thiol compounds each comprising a sulfur atom conjugated to said polymer such that said sulfur atom of said thiol compound and said thiol group of said therapeutic agent can form a disulfide bond; and
   c) a cell uptake promoter conjugated to said polymer.

2. The carrier of claim 1, wherein said polymer comprises a branched or linear structure.

3. The carrier of claim 1, wherein said polymer is a water soluble polymer.

4. The carrier of claim 3, wherein said water soluble polymer is selected from the group consisting of polyethylene glycol, carboxymethylcellulose, dextran, polyvinyl alcohol, polyvinyl pyrrolidone, poly-1,3-dioxolane, poly-1,3,6-trioxane, amino acid homopolymers, polypropylene glycol, copolymers of ethylene glycol/propylene glycol, ethylene/maleic anhydride copolymer, amino acid copolymers, copolymers of polyethylene glycol and an amino acid, polypropylene oxide/ethylene oxide copolymers, and polyethylene glycol/thiomalic acid copolymers.

5. The carrier of claim 1, wherein said polymer has a molecular weight ranging from about 1,000 to about 1,000,000 Daltons.

6. The carrier of claim 5, wherein said polymer has a molecular weight of about 20,000 to about 200,000 Daltons.

7. The carrier of claim 1, wherein said multiple thiol compounds are attached to said polymer at an interval.

8. The carrier of claim 7, wherein said interval is about 100 to about 10,000 Daltons.

9. The carrier of claim 1, wherein said polymer comprises multiple functional groups attached to said polymer and available for reaction with said thiol compound, so that said multiple thiol compounds are conjugated to said multiple functional groups.

10. The carrier of claim 9, wherein said multiple functional groups are attached to said polymer at an interval.

11. The carrier of claim 10, wherein said interval is about 100 to about 10,000 Daltons.

12. The carrier of claim 11, wherein said functional group comprises a ketone, an ester, a carboxylic acid, an aldehyde, an alcohol, a thiol, or an amine.

13. The carrier of claim 1, wherein said thiol compound comprises cysteamine, 1-amino-2-methyl-2-propanethiol, or 1-amino-2-propanethiol.

14. The carrier of claim 1, further comprising a cell uptake promoter conjugated to said polymer.

15. The carrier of claim 1, wherein said cell uptake promoter is biotin.

16. A conjugate for in-vivo delivery of a therapeutic agent comprising a thiol group, wherein said conjugate comprises:
   a) a polymer;
   b) multiple thiol compounds each comprising a sulfur atom conjugated to said polymer such that said sulfur atom of said thiol compound and said thiol group of said therapeutic agent can form a disulfide bond: and
   c) a therapeutic agent comprising a thiol group bound to said polymer through said disulfide bond, wherein said therapeutic agent comprising a thiol group, further comprises a cell uptake promoter conjugated thereto.

17. The conjugate of claim 16, wherein said cell uptake promoter conjugated to said therapeutic agent is biotin.

18. The conjugate of claim 1, wherein said therapeutic agent comprising a thiol group comprises a Tat-inhibitory polypeptide, comprising an amino acid sequence of formula I:

R-Arg-Lys-Lys-Arg-Arg-Gln-Arg-Arg-Arg-X-(biotin)-Cys-NH$_2$ (SEQ ID NO:1), biologically or pharmaceutically acceptable salts thereof, or stereo, optical or geometrical isomers thereof, as well as the pharmaceutically acceptable salts or solvates thereof, wherein
R comprises the residue of a carboxylic acid or an acetyl group; and
X is a Cys or Lys residue.

19. The conjugate of claim 18, wherein said therapeutic agent comprising a thiol compound comprises an amino acid sequence of:
   N-acetyl-Arg-Lys-Lys-Arg-Arg-Gln-Arg-Arg-Arg-Cys-(biotin)-Cys-NH$_2$ (SEQ ID NO:2)
   N-acetyl-Arg-Lys-Lys-Arg-Arg-Gln-Arg-Arg-Lys-(biotin)-Cys-NH$_2$ (SEQ ID NO:3)
   N-acetyl-Arg-Lys-Lys-Arg-Arg-Gln-Arg-Arg-Arg-D-Cys-biotin)-Cys-NH$_2$ (SEQ ID NO:4)
   N-acetyl-Arg-Lys-Lys-Arg-Arg-Gln-Arg-Arg-Arg-D-Lys-(biotin)-Cys-NH$_2$ (SEQ ID NO: 5)
   N-acetyl-Gln-Lys-Lys-Arg-Arg-Gln-Arg-Arg-Arg-D-Lys-(biotin)-Cys-NH$_2$ (SEQ ID NO:6) or
   N-acetyl-Arg-Lys-Lys-Arg-Arg-Pro-Arg-Arg-Arg-Cys-(biotin)-Cys-NH$_2$ (SEQ ID NO:7).

20. The conjugate of claim 1, wherein said therapeutic agent comprising a thiol group comprises a Tat-inhibitory polypeptide, comprising an amino acid sequence of SEQ ID NO:8:
   N-acetyl-DCys-DLys-(biotin)-DArg-DArg-DArg-DGln-DArg-DArg-DLys-DLys-DArg-NH$_2$, or biologically or pharmaceutically acceptable salts thereof.

21. A method of making a carrier for in-vivo delivery of a therapeutic agent comprising a thiol group, wherein the carrier comprises a polymer and multiple disulfide compounds conjugated thereto, each said disulfide compound comprising a first sulfur atom conjugated to a sulfur atom of a stable leaving group such that said first sulfur atom and the thiol group of the therapeutic agent can form a disulfide bond, wherein the method comprises the steps of:
   a) reacting a thiol compound with a second disulfide compound comprising two stable leaving group to form a first intermediate wherein a sulfur atom of the thiol compound and a sulfur atom of the disulfide bond of the second disulfide compound form a disulfide bond; and
   b) reacting multiple said first intermediates with said polymer to form the carrier, wherein said multiple first intermediates are conjugated to the polymer, so that the sulfur atoms of the multiple disulfide compounds and the thiol group of the therapeutic agent can form a disulfide bond.

22. The method of claim 21, wherein the second disulfide compound of step (a) is symmetric.

23. The method of claim 22, wherein said disulfide compound is 2,2'-dithiodipyridine.

24. The method of claim 21, wherein the polymer comprises a branched or linear structure.

25. The method of claim 21, wherein the polymer is a water soluble polymer.

26. The method of claim 25, wherein the polymer comprises polyethylene glycol, carboxymethylcellulose, dextran, polyvinyl alcohol, polyvinyl pyrrolidone, poly-1,3-dioxolane, poly-1,3,6-trioxane, amino acid homopolymers, polypropylene glycol, copolymers of ethylene glycol/propylene glycol, ethylene/maleic anhydride copolymer, amino acid copolymers, copolymers of polyethylene glycol and an amino acid, polypropylene oxide/ethylene oxide copolymers, or polyethylene glycol/thiomalic acid copolymers.

27. The method of claim 21, wherein the polymer has a molecular weight ranging from about 1,000 to about 1,000,000 Daltons.

28. The method of claim 27, wherein the polymer has a molecular weight of about 20,000 to about 200,000 Daltons.

29. The method of claim 21, wherein the multiple disulfide compounds are conjugated to the polymer at an interval.

30. The method of claim 29, wherein the interval is about 100 to about 10,000 Daltons.

31. The method of claim 21, wherein the thiol compound comprises cysteamine, 1-amino-2-methyl-2-propanethiol, or 1-amino-2-propanethiol.

32. The method of claim 21, further comprising the step of conjugating a cell uptake promoter to the polymer prior to reacting the polymer with the first intermediate.

33. The method of claim 32, wherein said cell uptake promoter is biotin.

34. The method of claim 21, wherein said polymer comprises multiple functional groups attached thereto available for reaction, and step b) comprises reacting the first intermediate with the polymer comprising multiple functional groups to form the carrier, wherein the first intermediate is conjugated to the multiple functional groups attached to the polymer.

35. The method of claim 34, wherein the multiple functional groups are attached to the polymer at an interval.

36. The method of claim 35, wherein the interval is about 100 to about 10,000 Daltons.

37. The method of claim 35, wherein the multiple functional groups comprise a ketone, an ester, a carboxylic acid, and aldehyde, an alcohol, a thiol, or an amine.

38. The method of claim 21, wherein a cell uptake promoter is conjugated to the therapeutic agent.

39. The method of claim 38, wherein said cell uptake promoter is biotin.

40. The method of claim 39, wherein said therapeutic agent comprising a thiol group comprises a Tat-inhibitory polypeptide comprising a polypeptide of the formula I:

R-Arg-Lys-Lys-Arg-Arg-Gln-Arg-Arg-Arg-X-(biotin) Cys-NH$_2$ (SEQ ID NO:1), biologically or pharmaceutically acceptable salts thereof, or stereo, optical or geometrical isomers thereof or pharmaceutically acceptable salts thereof, wherein
R comprises the residue of a carboxylic acid or an acetyl group; and
X is a Cys or Lys residue.

41. The method of claim 40, wherein said therapeutic agent comprises an amino acid sequence of:

N-acetyl-Arg-Lys-Lys-Arg-Arg-Gln-Arg-Arg-Arg-Cys-(biotin)-Cys-NH$_2$ (SEQ IDNO:2)

N-acetyl-Arg-Lys-Lys-Arg-Arg-Gln-Arg-Arg-Arg-Lys-(biotin)-Cys-NH$_2$ (SEQ ID NO:3)

N-acetyl-Arg-Lys-Lys-Arg-Arg-Gln-Arg-Arg-Arg-D-Cys-(biotin)-Cys-NH$_2$ (SEQ ID NO:4)

N-acetyl-Arg-Lys-Lys-Arg-Arg-Gln-Arg-Arg-Arg-D-Lys-(biotin)-Cys-NH$_2$ (SEQ ID NO:5)

N-acetyl-Gln-Lys-Lys-Arg-Arg-Gln-Arg-Arg-Arg-D-Lys-(biotin)-Cys-NH$_2$ (SEQ ID NO:6) or N-acetyl-Arg-Lys-Lys-Arg-Arg-Pro-Arg-Arg-Arg-Cys (biotin)-Cys-NH$_2$ (SEQ ID NO:7).

42. The method of claim 39, wherein said therapeutic agent comprises a Tat-inhibitory binding protein comprising an amino acid sequence of SEQ ID NO:8:

N-acetyl-DCys-DLys-(biotin)-DArg-DArg-DArg-DGln-DArg-DArg-DLys-DLys-DArg-NH$_2$, or biologically or pharmaceutically acceptable salts thereof.

43. A method of making a carrier for in-vivo delivery of a therapeutic agent comprising a thiol group, wherein the carrier comprises a polymer and multiple disulfide compounds conjugated thereto, each said disulfide compound comprising a first sulfur atom conjugated to a sulfur atom of a stable leaving group such that said first sulfur atom and the thiol group of the therapeutic agent can form a disulfide bond, wherein the method comprises the steps of:
a) reacting a first thiol compound with a second thiol compound to form a first intermediate, wherein a thiol group of the first thiol compound and a thiol group of the second thiol compound form a disulfide bond;
b) reacting multiple said first intermediates with a polymer to form a second intermediate, wherein multiple said first intermediates are conjugated to the polymer;
c) reducing the disulfide bond of the second intermediate to form a third intermediate comprising the polymer and the multiple first thiol compounds conjugated thereto so that the thiol groups of the first thiol compounds are is available for reaction; and
d) reacting the third intermediate with a disulfide compound comprising two stable leaving groups to form the carrier, wherein the sulfur atom of the first thiol compound and a sulfur atom of the a leaving group form a disulfide bond, so that the sulfur atom of the first thiol compound and the thiol group of the therapeutic agent can form a disulfide bond.

44. The method of claim 43, wherein the disulfide compound of step (d) is symmetric.

45. The method of claim 44, wherein said disulfide compound is 2,2'-dithiodipyridine.

46. The method of claim 43, wherein the polymer comprises a branched or linear structure.

47. The method of claim 43, wherein the polymer is a water soluble polymer.

48. The method of claim 47, wherein the polymer comprises polyethylene glycol, carboxymethylcellulose, dextran, polyvinyl alcohol, polyvinyl pyrrolidone, poly-1,3-dioxolane, poly-1,3,6-trioxane, amino acid homopolymers, polypropylene glycol, copolymers of ethylene glycol/propylene glycol, ethylene/maleic anhydride copolymer, amino acid copolymers, copolymers of polyethylene glycol and an amino acid, polypropylene oxide/ethylene oxide copolymers, or polyethylene glycol/thiomalic acid copolymers.

49. The method of claim 43, wherein the polymer has a molecular weight ranging from about 1,000 to about 1,000,000 Daltons.

50. The method of claim 49, wherein the polymer has a molecular weight of about 20,000 to about 200,000 Daltons.

51. The method of claim 43, wherein the multiple disulfide compounds are conjugated to the polymer at an interval.

52. The method of claim 51, wherein the interval is about 100 to about 10,000 Daltons.

53. The method of claim 43, wherein the polymer comprises multiple functional groups attached thereto, and step b) comprises reacting the first intermediate with the polymer comprising multiple functional groups attached thereto to form a second intermediate, wherein the first intermediate is conjugated to the multiple functional groups.

54. The method of claim 53, wherein the multiple functional groups are attached to the polymer at an interval.

55. The method of claim 54, wherein the interval is about 100 to about 10,000 Daltons.

56. The method of claim 54, wherein the multiple functional groups comprise a ketone, an ester, a carboxylic acid, an aldehyde, an alcohol, a thiol, or an amine.

57. The method of claim 43, wherein the thiol compound comprises cysteamine, 1-amino-2-methyl-2-propanethiol, or 1-amino-2-propanethiol.

58. The method of claim 43, further comprising the step of conjugating a cell uptake promoter to the polymer prior to reacting the polymer with the first intermediate.

59. The method of claim 58, wherein said cell uptake promoter is biotin.

60. A carrier for in-vivo delivery of a therapeutic agent comprising a thiol group, wherein said carrier comprises:
   a) a polymer;
   b) multiple thiol compounds conjugated to said polymer, said thiol compounds comprising a sulfur atom and at least one functional group; and
   c) a cell uptake promoter conjugated to said polymer, such that said sulfur atom of said thiol compounds and said thiol group of said therapeutic agent can form a disulfide bond, and the rate at which the disulfide bond is reduced in vivo so that said therapeutic agent is released from the carrier, is dependent on the size of the functional group attached to the thiol compound.

61. A method of treating a viral infection in a mammal, comprising administering to the mammal a therapeutically effective amount of a carrier for in-vivo delivery of a therapeutic agent comprising a thiol group, wherein the carrier comprises:
   a) a polymer; and
   b) at least one thiol compound conjugated to said polymer such that said thiol group of said thiol compound and said thiol group of said therapeutic agent form a disulfide bond, and
wherein the therapeutic agent is a Tat-inhibitory polypeptide.

62. The method of claim 61, wherein said Tat-inhibitory polypeptide derivative comprises:
   R-Arg-Lys-Lys-Arg-Arg-Gln-Arg-Arg-Arg-X-(biotin)-Cys-NH$_2$ (SEQ ID NO:1), or pharmaceutically acceptable salts thereof, or stereo, optical or geometrical isomers thereof or pharmaceutically acceptable salts or solvates thereof, wherein
      R comprises the residue of a carboxylic acid or an acetyl group; and
      X is a Cys or Lys residue.

63. The method of claim 62, wherein said Tat-inhibitory polypeptide derivative comprises an amino acid sequence of:
   N-acetyl-Arg-Lys-Lys-Arg-Arg-Gln-Arg-Arg-Arg-Cys-(biotin)-Cys-NH$_2$(SEQ IDNO:2)
   N-acetyl-Arg-Lys-Lys-Arg-Arg-Gln-Arg-Arg-Arg-Lys-(biotin)-Cys-NH$_2$(SEQ ID NO:3)
   N-acetyl-Arg-Lys-Lys-Arg-Arg-Gln-Arg-Arg-Arg-D-Cys-(biotin)-Cys-NH$_2$(SEQ ID NO :4)
   N-acetyl-Arg-Lys-Lys-Arg-Arg-Gln-Arg-Arg-Arg-D-Lys-(biotin)-Cys-NH$_2$(SEQ ID NO: 5)
   N-acetyl-Gln-Lys-Lys-Arg-Arg-Gln-Arg-Arg-Arg-D-Lys-(biotin)-Cys-NH$_2$(SEQ ID NO:6) or
   N-acetyl-Arg-Lys-Lys-Arg-Arg-Pro-Arg-Arg-Arg-Cys (biotin)-Cys-NH$_2$(SEQ ID NO:7).

64. The method of claim 61, wherein said Tat-inhibitory polypeptide comprises an amino acid sequence of SEQ ID NO:8:
   N-acetyl-DCys-DLys-(biotin)-DArg-DArg-DArg-DGln-DArg-DArg-DLys-DLys-DArg-NH$_2$ or biologically or pharmaceutically acceptable salts thereof.

65. The method of any of claims 61, 62, 63, or 64, wherein said viral infection is Aids.

66. The method of claim 65, wherein said mammal comprises humans.

67. The carrier of claim 6 wherein said polymer has a molecular weight of about 27,000 Daltons.

68. The carrier of claim 8 wherein said interval is about 300 to about 3,000 Daltons.

69. The carrier of claim 11 wherein said interval is about 300 to about 3,000 Daltons.

70. The method of claim 28 wherein the polymer has a molecular weight of about 27,000 Daltons.

71. The method of claim 30 wherein said interval is about 300 to about 3,000 Daltons.

72. The method of claim 36 wherein said interval is about 300 to about 3,000 Daltons.

73. The method of claim 50 wherein the polymer has a molecular weight of about 27,000 Daltons.

74. The method of claim 52 wherein said interval is about 300 to about 3,000 Daltons.

75. The method of claim 55 wherein said interval is about 300 to about 3,000 Daltons.

76. The method of claim 1 wherein said therapeutic agent comprising a thiol group is a Tat inhibitory peptide.

77. The conjugate of claim 16, wherein said polymer comprises a branched or linear structure.

78. The conjugate of claim 16, wherein said polymer is a water soluble polymer.

79. The conjugate of claim 78, wherein said water soluble polymer is selected from the group consisting of polyethylene glycol, carboxymethylcellulose, dextran, polyvinyl alcohol, polyvinyl pyrrolidone, poly-1,3-dioxolane, poly-1, 3,6trioxane, amino acid homopolymers, polypropylene glycol, copolymers of ethylene glycol/propylene glycol, ethylene/maleic anhydride co polymer, amino acid copolymers, copolymers of polyethylene glycol and an amino acid, polypropylene oxide/ethylene oxide copolymers, and polyethylene glycol/thiomalic acid copolymers.

80. The conjugate of claim 16, wherein said polymer has a molecular weight ranging from about 1,000 to about 1,000,000 Daltons.

81. The conjugate of claim 80, wherein said polymer has a molecular weight of about 20,000 to about 200,000 Daltons.

82. The conjugate of claim 81 wherein said polymer has a molecular weight of about 27,000 Daltons.

83. The conjugate of claim 16, wherein said multiple thiol compounds are attached to said polymer at an interval.

84. The conjugate of claim 83, wherein said interval is about 100 to about 10,000 Daltons.

85. The conjugate of claim 84, wherein said interval is about 300 to about 3,000 Daltons.

86. The conjugate of claim 16, wherein said polymer comprises multiple functional groups attached to said polymer and available for reaction with said thiol compound, so that said multiple thiol compounds are conjugated to said multiple functional groups.

87. The conjugate of claim 86 wherein said multiple functional groups are attached to said polymer at an interval.

88. The conjugate of claim 87, wherein said interval is about 100 to about 10,000 Daltons.

89. The conjugate of claim 86, wherein said functional group comprises a ketone, an ester, a carboxylic acid, an aldehyde, an alcohol, a thiol, or an amine.

90. The conjugate of claim 16, wherein said thiol compound comprises cysteamine, 1-amino-2-methyl-2-propanethiol, or 1-amino-2-propanethiol.

91. A conjugate for in-vivo delivery of a therapeutic agent comprising a thiol group, wherein said conjugate comprises:

a) a polymer and a cell uptake promoter conjugated thereto;

b) multiple thiol compounds each comprising a sulfur atom conjugated to said polymer such that said sulfur atom of said thiol compound and said thiol group of said therapeutic agent can form a disulfide bond; and c) a therapeutic agent comprising a thiol group bound to said polymer through said disulfide bond.

92. The conjugate of claim 91, wherein said polymer comprises a branched or linear structure.

93. The conjugate of claim 91, wherein said polymer is a water soluble polymer.

94. The conjugate of claim 93, wherein said water soluble polymer is selected from the group consisting of polyethylene glycol, carboxymethylcellulose, dextran, polyvinyl alcohol, polyvinyl pyrrolidone, poly-1,3-dioxolane, poly-1,3,6-trioxane, amino acid homopolymers, polypropylene glycol, copolymers of ethylene glycol/propylene glycol, ethylene/maleic anhydride copolymer, amino acid copolymers, copolymers of polyethylene glycol and an amino acid, polypropylene oxide/ethylene oxide copolymers, and polyethylene glycol/thiomalic acid copolymers.

95. The conjugate of claim 91, wherein said polymer has a molecular weight ranging from about 1,000 to about 1,000,000 Daltons.

96. The conjugate of claim 95, wherein said polymer has a molecular weight of about 20,000 to about 200,000 Daltons.

97. The conjugate of claim 96 wherein said polymer has a molecular weight of about 27,000 Daltons.

98. The conjugate of claim 91, wherein said multiple thiol compounds are attached to said polymer at an interval.

99. The conjugate of claim 98, wherein said interval is about 100 to about 10,000 Daltons.

100. The conjugate of claim 99 wherein said interval is about 300 to about 3,000 Daltons.

101. The conjugate of claim 91, wherein said thiol compound comprises cysteamine, 1-amino-2-methyl-2-propanethiol, or 1-amino-2-propanethiol.

102. The conjugate of claim 91, wherein said polymer comprises multiple functional groups attached to said polymer and available for reaction with said thiol compound, so that said multiple thiol compounds are conjugated to said multiple functional groups.

103. The conjugate of claim 102 wherein said multiple functional groups are attached to said polymer at an interval.

104. The conjugate of claim 103, wherein said interval is about 100 to about 10,000 Daltons.

105. The conjugate of claim 104, wherein said functional group comprises a ketone, an ester, a carboxylic acid, an aldehyde, an alcohol, a thiol, or an amine.

106. The conjugate of claim 91, wherein said cell uptake promoter is biotin.

107. The conjugate of claim 91, wherein said therapeutic agent comprising a thiol group comprises a Tat-inhibitory polypeptide, comprising an amino acid sequence of formula I: R-Arg-Lys-Lys-Arg-Arg-Gln-Arg-Arg-Arg-X-(biotin)-Cys-NH$_2$ (SEQ ID NO: 1), biologically or pharmaceutically acceptable salts thereof, or stereo, optical or geometrical isomers thereof, as well as the pharmaceutically acceptable salts or solvates thereof, wherein R comprises the residue of a carboxylic acid or an acetyl group; and X is a Cys or Lys residue.

108. The conjugate of claim 91, wherein said therapeutic agent comprising a thiol compound comprises an amino acid sequence of:

N-acetyl-Arg-Lys-Lys-Arg-Arg-Gln-Arg-Arg-Arg-Cys-(biotin)-Cys-NH$_2$ (SEQ ID NO: 2)

N-acetyl-Arg-Lys-Lys-Arg-Arg-Gln-Arg-Arg-Arg-Lys-(biotin)-Cys-NH$_2$ (SEQ ID NO:3)

N-acetyl-Arg-Lys-Lys-Arg-Arg-Gln-Arg-Arg-Arg-D-Cys-(biotin)-Cys-NH$_2$ (SEQ ID NO:4)

N-acetyl-Arg-Lys-Lys-Arg-Arg-Gln-Arg-Arg-Arg-D-Lys-(biotin)-Cys-NH$_2$ (SEQ ID NO:5)

N-acetyl-Gln-Lys-Lys-Arg-Arg-Gln-Arg-Arg-Arg-D-Lys-(biotin)-Cys-NH$_2$ (SEQ ID NO:6) or N-acetyl-Arg-Lys-Lys-Arg-Arg-Pro-Arg-Arg-Arg-Cys-(biotin)-Cys-NH$_2$ (SEQ ID NO:7).

109. The conjugate of claim 91, wherein said therapeutic agent comprising a thiol group comprises a Tat-inhibitory polypeptide, comprising an amino acid sequence of SEQ ID NO:8:

N-acetyl-DCys-DLys-(biotin)-DArg-DArg-DArg-DGln-DArg-DArg-DLys-DLys-DArg-NH$_2$ or biologically or pharmaceutically acceptable salts thereof.

110. A method for intracellular delivery of a therapeutic agent comprising a thiol group comprising contacting a cell with an effective intracellular delivery promoting amount of a conjugate of claim 16.

111. A method for intracellular delivery of a therapeutic agent comprising a thiol group comprising contacting a cell with an effective intracellular delivery promoting amount of a conjugate of claim 91.

* * * * *

UNITED STATES PATENT AND TRADEMARK OFFICE
CERTIFICATE OF CORRECTION

PATENT NO.     : 6,258,774 B1
DATED          : July 10, 2001
INVENTOR(S)    : Stein et al.

It is certified that error appears in the above-identified patent and that said Letters Patent is hereby corrected as shown below:

Title page,
Item [73], should read -- Assignees: University of Medicine and Dentistry of New Jersey, and Rutgers, the State University of New Jersey, both of Piscataway, NJ (US) --

Signed and Sealed this

Seventh Day of January, 2003

JAMES E. ROGAN
*Director of the United States Patent and Trademark Office*

SEQUENCE LISTING

<160> NUMBER OF SEQ ID NOS: 10

<210> SEQ ID NO: 1
<211> LENGTH: 11
<212> TYPE: PRT
<213> ORGANISM: Human immunodeficiency virus type 1
<220> FEATURE:
<223> OTHER INFORMATION: Internal sequence from the Tat protein, but
      with an extra Cys not found in natural protein.
<220> FEATURE:
<221> NAME/KEY: SITE
<222> LOCATION: (10)
<223> OTHER INFORMATION: Xaa is either Cys(biotin) or Lys(biotin) at
      this position.
<220> FEATURE:
<221> NAME/KEY: BINDING
<222> LOCATION: (10)
<223> OTHER INFORMATION: Either Cys(biotin) or Lys(biotin) at this
      position.
<220> FEATURE:
<223> OTHER INFORMATION: Peptide has an N-terminal carboxylic acid
      residue.
<220> FEATURE:
<223> OTHER INFORMATION: Peptide has a C-terminal amide group.

<400> SEQUENCE: 1

Arg Lys Lys Arg Arg Gln Arg Arg Arg Xaa Cys
 1               5                  10

<210> SEQ ID NO: 2
<211> LENGTH: 11
<212> TYPE: PRT
<213> ORGANISM: Human immunodeficiency virus type 1
<220> FEATURE:
<223> OTHER INFORMATION: Internal sequence from the Tat protein, but
      with two extra Cys residues not found in the natural protein.
<220> FEATURE:
<221> NAME/KEY: BINDING
<222> LOCATION: (10)
<223> OTHER INFORMATION: Cys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 2

Arg Lys Lys Arg Arg Gln Arg Arg Arg Cys Cys
 1               5                  10

<210> SEQ ID NO: 3
<211> LENGTH: 11
<212> TYPE: PRT
<213> ORGANISM: Human immunodeficiency virus type 1
<220> FEATURE:
<223> OTHER INFORMATION: Internal sequence from the Tat protein, but
      with an extra Lys and an extra Cys not found in the natural
      protein.
<220> FEATURE:
<221> NAME/KEY: BINDING
<222> LOCATION: (10)
<223> OTHER INFORMATION: Lys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 3

Arg Lys Lys Arg Arg Gln Arg Arg Arg Lys Cys
 1               5                  10

```
<210> SEQ ID NO: 4
<211> LENGTH: 11
<212> TYPE: PRT
<213> ORGANISM: Human immunodeficiency virus type 1
<220> FEATURE:
<223> OTHER INFORMATION: Internal sequence from the Tat protein, but
      with two extra Cys not found in the natural protein.
<220> FEATURE:
<221> NAME/KEY: SITE
<222> LOCATION: (10)
<223> OTHER INFORMATION: Cys is the D isomer at this position.
<220> FEATURE:
<221> NAME/KEY: BINDING
<222> LOCATION: (10)
<223> OTHER INFORMATION: D-Cys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 4

Arg Lys Lys Arg Arg Gln Arg Arg Arg Cys Cys
 1               5                  10

<210> SEQ ID NO: 5
<211> LENGTH: 11
<212> TYPE: PRT
<213> ORGANISM: Human immunodeficiency virus type 1
<220> FEATURE:
<223> OTHER INFORMATION: Internal sequence from the Tat protein, but
      with an extra Lys and an extra Cys not found in the natural
      protein.
<220> FEATURE:
<221> NAME/KEY: SITE
<222> LOCATION: (10)
<223> OTHER INFORMATION: Lys is D isomer at this position.
<220> FEATURE:
<221> NAME/KEY: BINDING
<222> LOCATION: (10)
<223> OTHER INFORMATION: D-Lys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 5

Arg Lys Lys Arg Arg Gln Arg Arg Arg Lys Cys
 1               5                  10

<210> SEQ ID NO: 6
<211> LENGTH: 11
<212> TYPE: PRT
<213> ORGANISM: Human immunodeficiency virus type 1
<220> FEATURE:
<223> OTHER INFORMATION: Same as Sequence ID 3, but with a substitution
      of Arg to Gln.
<220> FEATURE:
<221> NAME/KEY: SITE
<222> LOCATION: (10)
<223> OTHER INFORMATION: Lys is the D isomer at this position.
<220> FEATURE:
<221> NAME/KEY: BINDING
<222> LOCATION: (10)
<223> OTHER INFORMATION: D-Lys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 6

Gln Lys Lys Arg Arg Gln Arg Arg Arg Lys Cys
 1               5                  10
```

```
<210> SEQ ID NO: 7
<211> LENGTH: 11
<212> TYPE: PRT
<213> ORGANISM: Human immunodeficiency virus type 1
<220> FEATURE:
<223> OTHER INFORMATION: Same as Sequence ID 2, but with a substitution
      of Gln to Pro.
<220> FEATURE:
<221> NAME/KEY: BINDING
<222> LOCATION: (10)
<223> OTHER INFORMATION: Cys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 7

Arg Lys Lys Arg Arg Pro Arg Arg Arg Cys Cys
 1               5                  10

<210> SEQ ID NO: 8
<211> LENGTH: 11
<212> TYPE: PRT
<213> ORGANISM: Human immunodeficiency virus type 1
<220> FEATURE:
<223> OTHER INFORMATION: All amino acids in this sequence are D amino
      acid.
<220> FEATURE:
<221> NAME/KEY: BINDING
<222> LOCATION: (2)
<223> OTHER INFORMATION: D-Lys(biotin)
<220> FEATURE:
<223> OTHER INFORMATION: Peptide has an N-terminal acetyl group.
<220> FEATURE:
<223> OTHER INFORMATION: Peptide has a C-terminal amide group.

<400> SEQUENCE: 8

Cys Lys Arg Arg Arg Gln Arg Arg Lys Lys Arg
 1               5                  10

<210> SEQ ID NO: 9
<211> LENGTH: 5
<212> TYPE: PRT
<213> ORGANISM: Artificial Sequence
<220> FEATURE:
<223> OTHER INFORMATION: Description of Artificial Sequence: A Model
      Peptide
<220> FEATURE:
<223> OTHER INFORMATION: Peptide has an N-terminal acetyl group.
<220> FEATURE:
<223> OTHER INFORMATION: Peptidet has a C-terminal amide group.

<400> SEQUENCE: 9

Phe Arg Arg Arg Cys
 1               5

<210> SEQ ID NO: 10
<211> LENGTH: 10
<212> TYPE: PRT
<213> ORGANISM: Human immunodeficiency virus type 1
<220> FEATURE:
<223> OTHER INFORMATION: Peptide has an N-terminal acetyl group.
<220> FEATURE:
<223> OTHER INFORMATION: Peptide has a  C-terminal amide group.

<400> SEQUENCE: 10

Arg Lys Lys Arg Arg Gln Arg Arg Arg Cys
 1               5                  10
```